(12) United States Patent
Yang

(10) Patent No.: US 7,393,345 B2
(45) Date of Patent: Jul. 1, 2008

(54) STERILIZED SAFETY SYRINGE

(76) Inventor: Chang-Ming Yang, No. 27, Guangfu Rd., Junan Jen, Miaoli (TW)

( * ) Notice: Subject to any disclaimer, the term of this patent is extended or adjusted under 35 U.S.C. 154(b) by 632 days.

(21) Appl. No.: 10/621,331

(22) Filed: Jul. 18, 2003

(65) Prior Publication Data

US 2005/0015055 A1    Jan. 20, 2005

(51) Int. Cl.
*A61M 5/32* (2006.01)
(52) U.S. Cl. ........................................ 604/199; 604/198
(58) Field of Classification Search ................ 604/198, 604/199, 111, 195, 182, 192, 187, 141, 236; 222/334, 389
See application file for complete search history.

(56) References Cited

U.S. PATENT DOCUMENTS

| 4,243,035 A * | 1/1981 | Barrett ........................... 604/1 |
| 5,015,237 A * | 5/1991 | Kleinwolterink et al. .... 604/143 |
| 6,679,864 B2 * | 1/2004 | Gagnieux et al. ........... 604/198 |

\* cited by examiner

*Primary Examiner*—Nicholas D. Lucchesi
*Assistant Examiner*—Christopher D Koharski
(74) *Attorney, Agent, or Firm*—Banger Shia

(57) ABSTRACT

A sterilized safety syringe including a syringe tube, a protective cover, a sterilizer, and an air compressor. The protective cover is slid into a guide slot of the syringe tube with several sliding plates whose rear ends are are in close contact with the wall of the guide slot. The syringe tube is equipped with several air conducting pipes which are connected with corresponding air feeding pipes of an air compressor. A plug is formed at the rear end of the sterilizer which is plugged into a drilled hole formed on the protective cover.

2 Claims, 33 Drawing Sheets

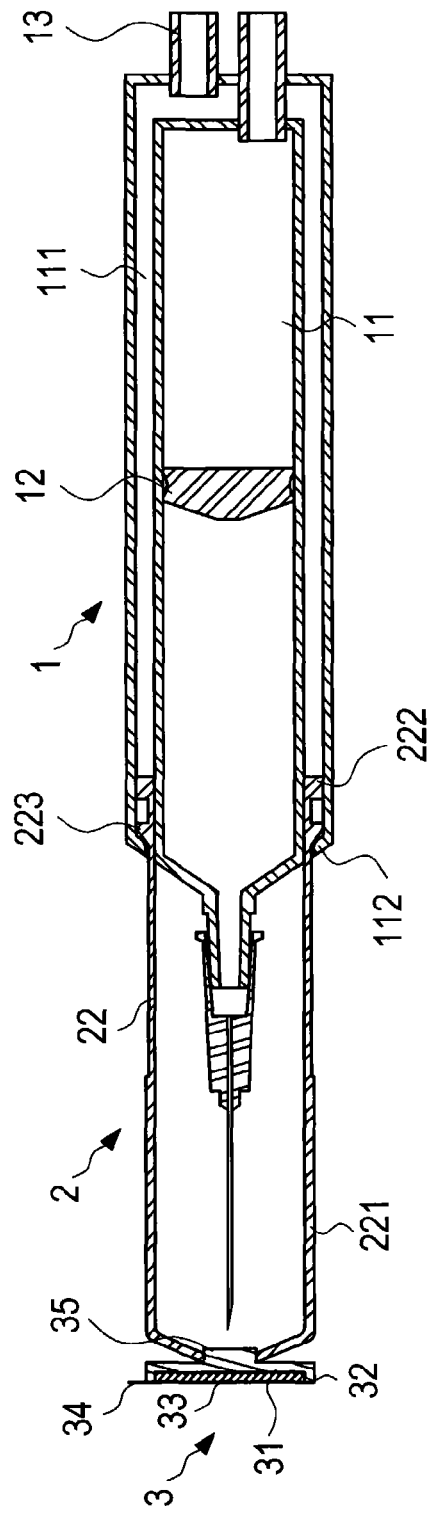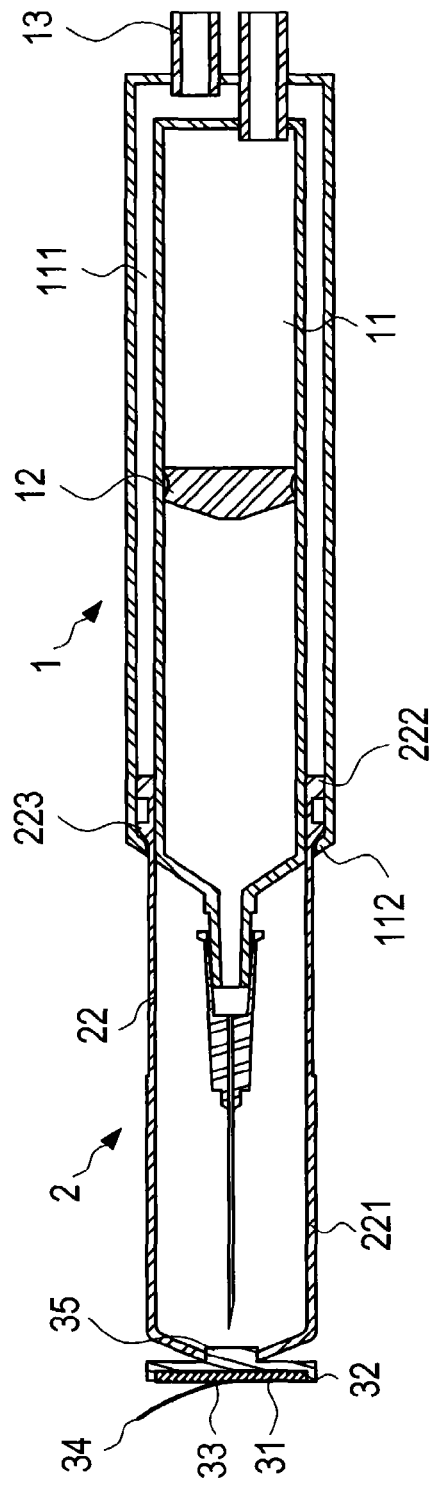

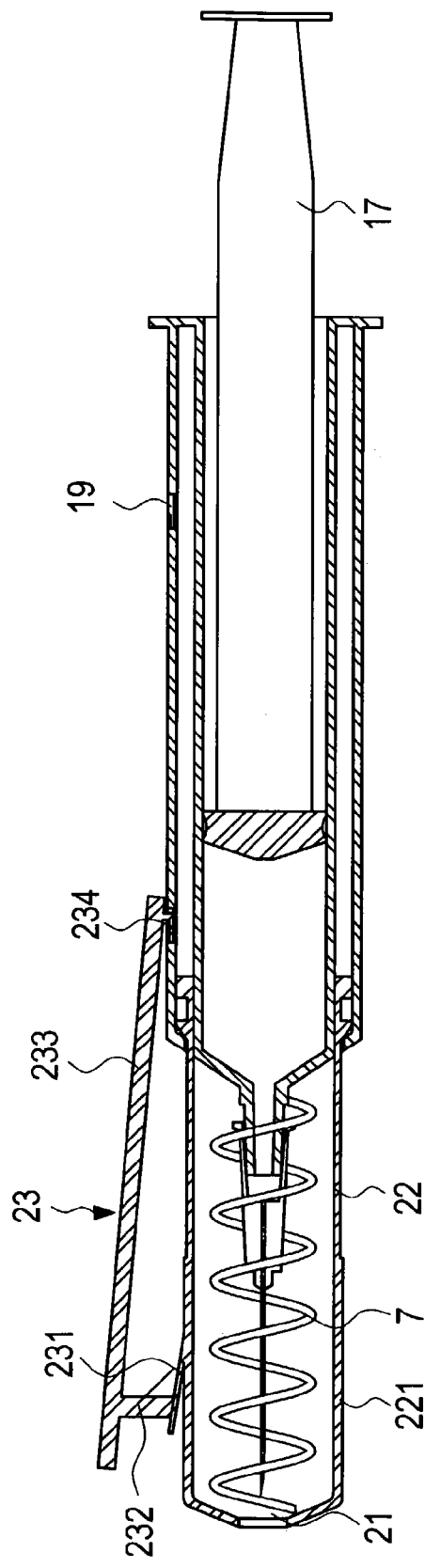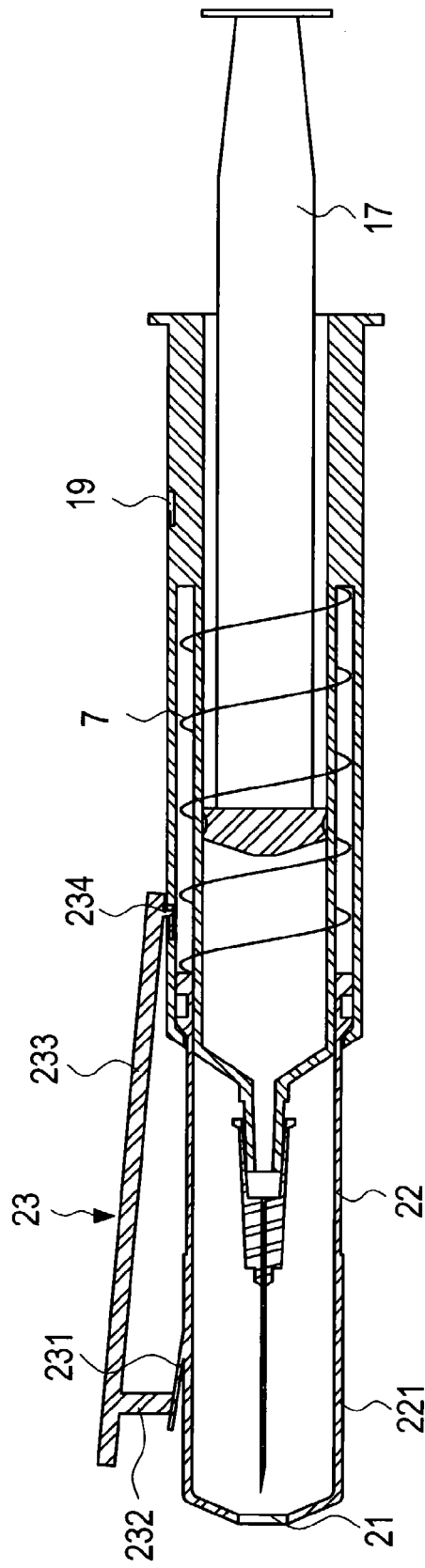
FIG. 26
FIG. 27

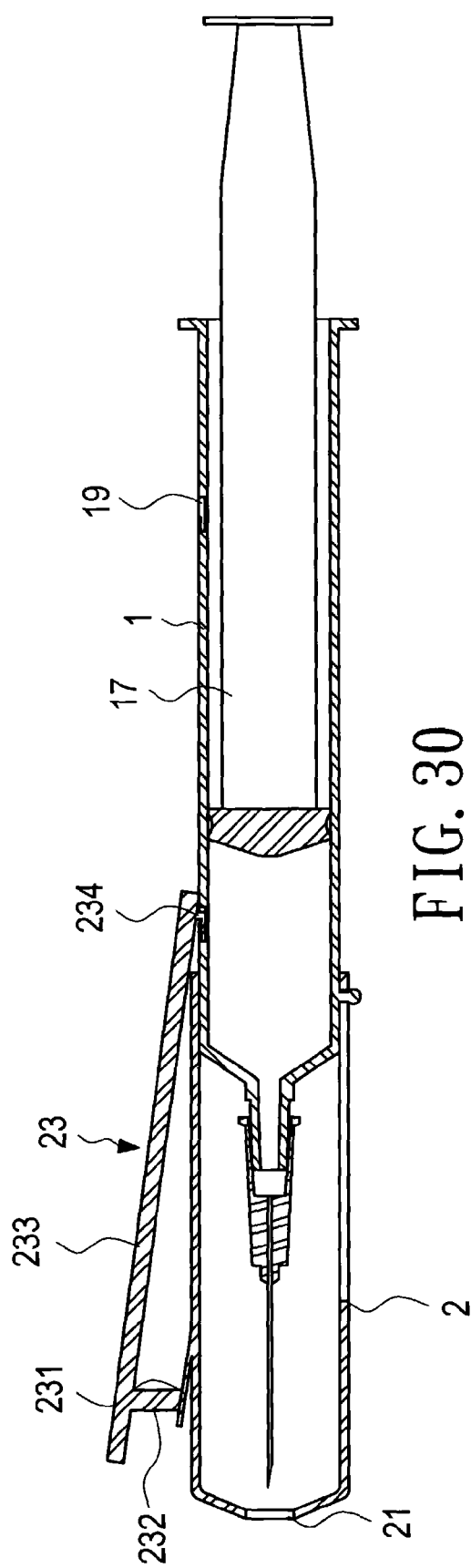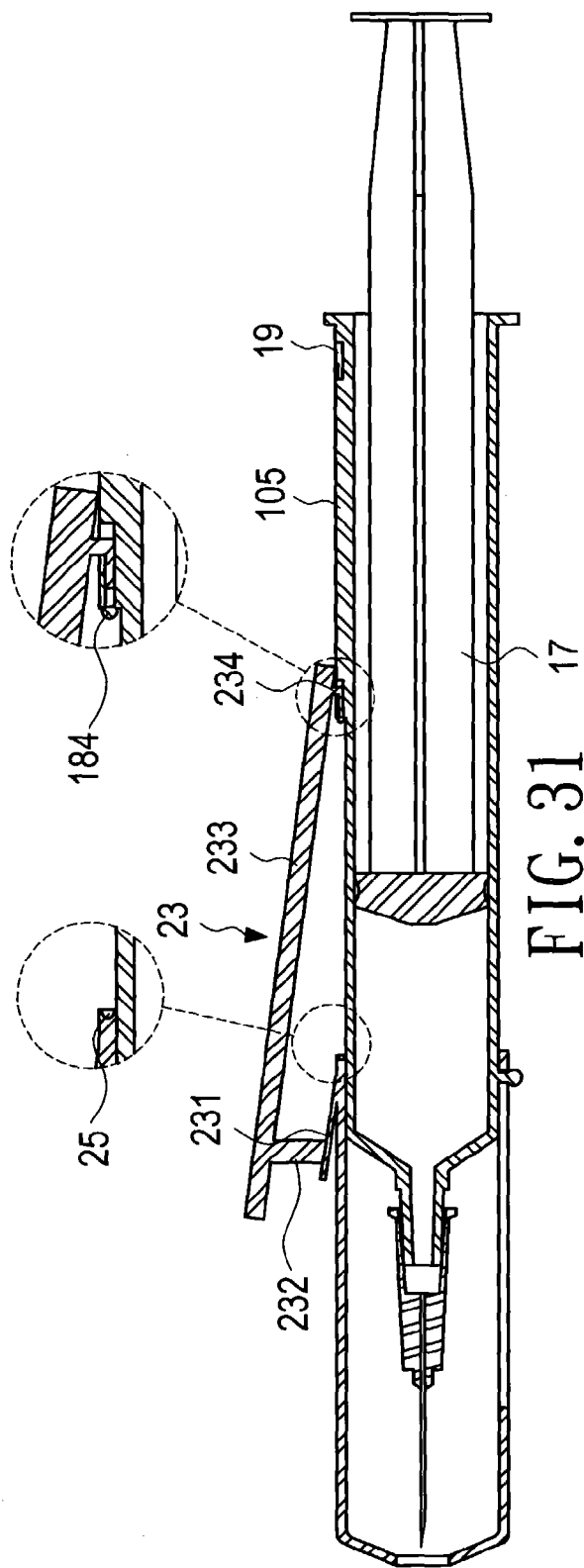
FIG. 30
FIG. 31

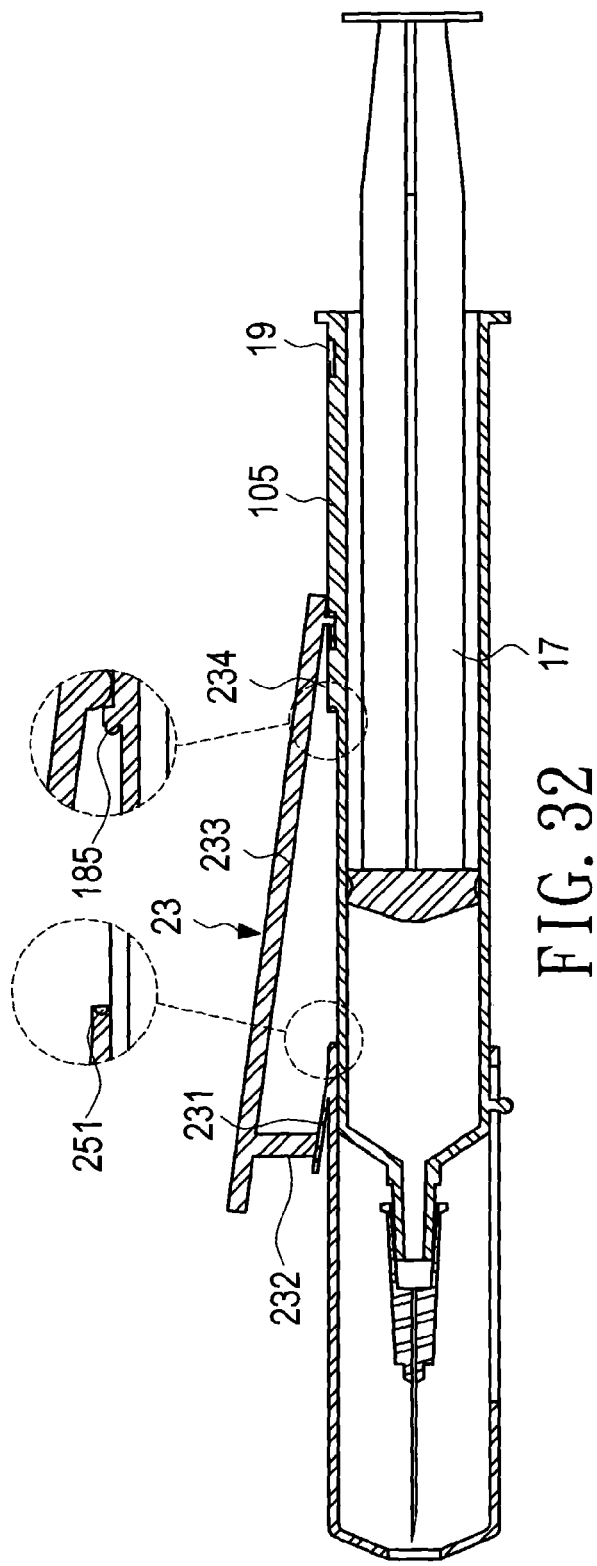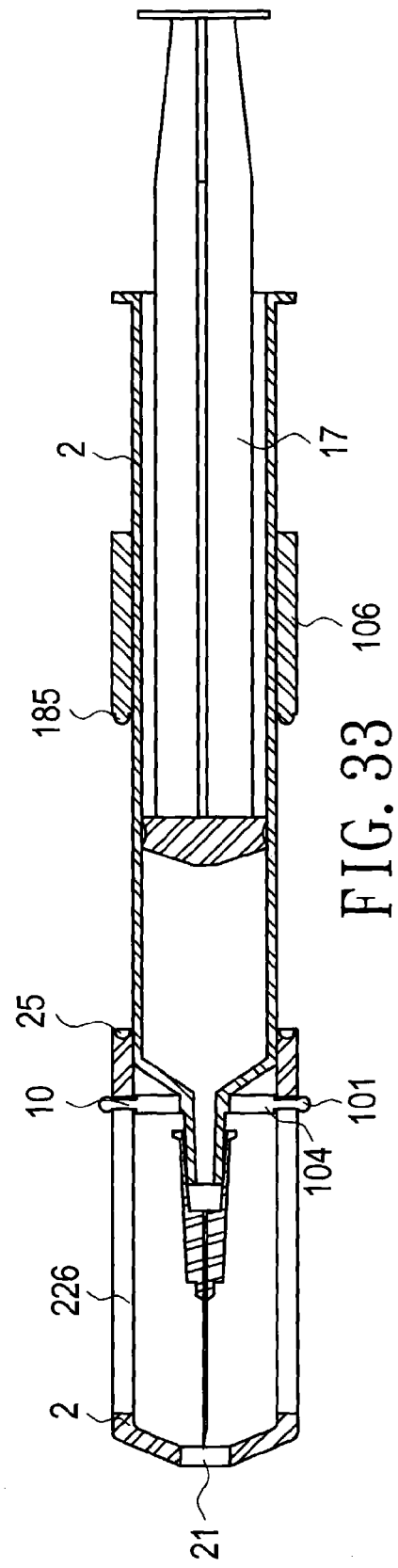

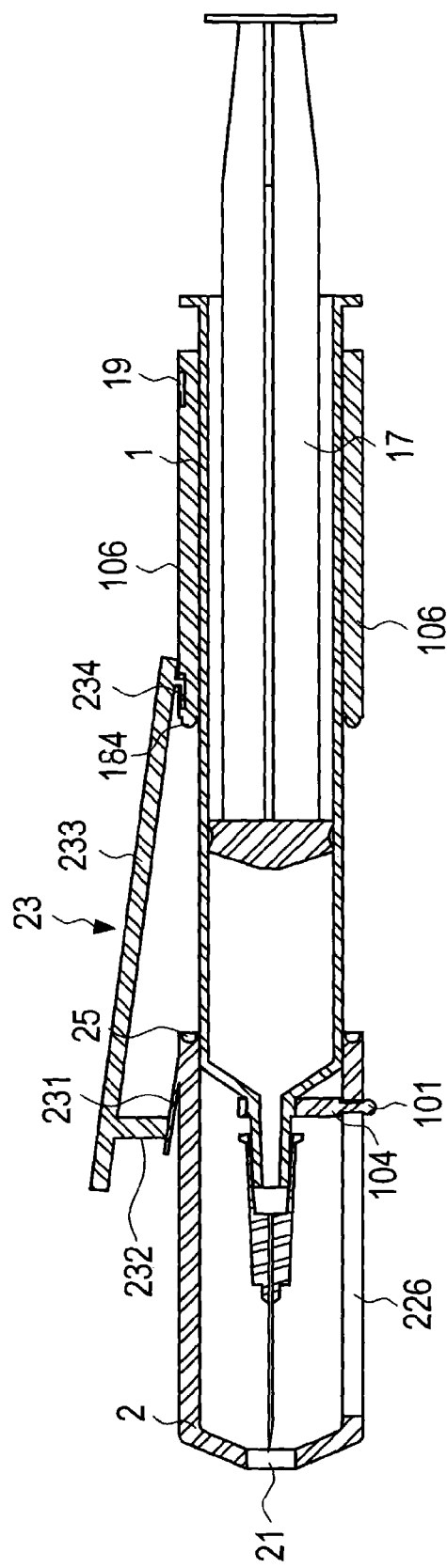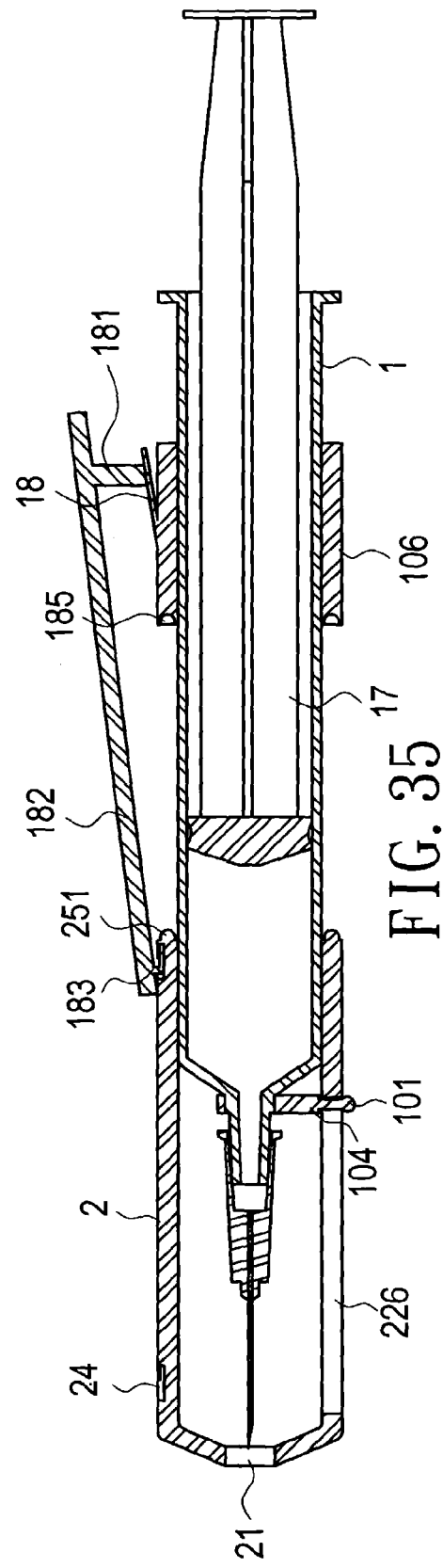
FIG. 34
FIG. 35

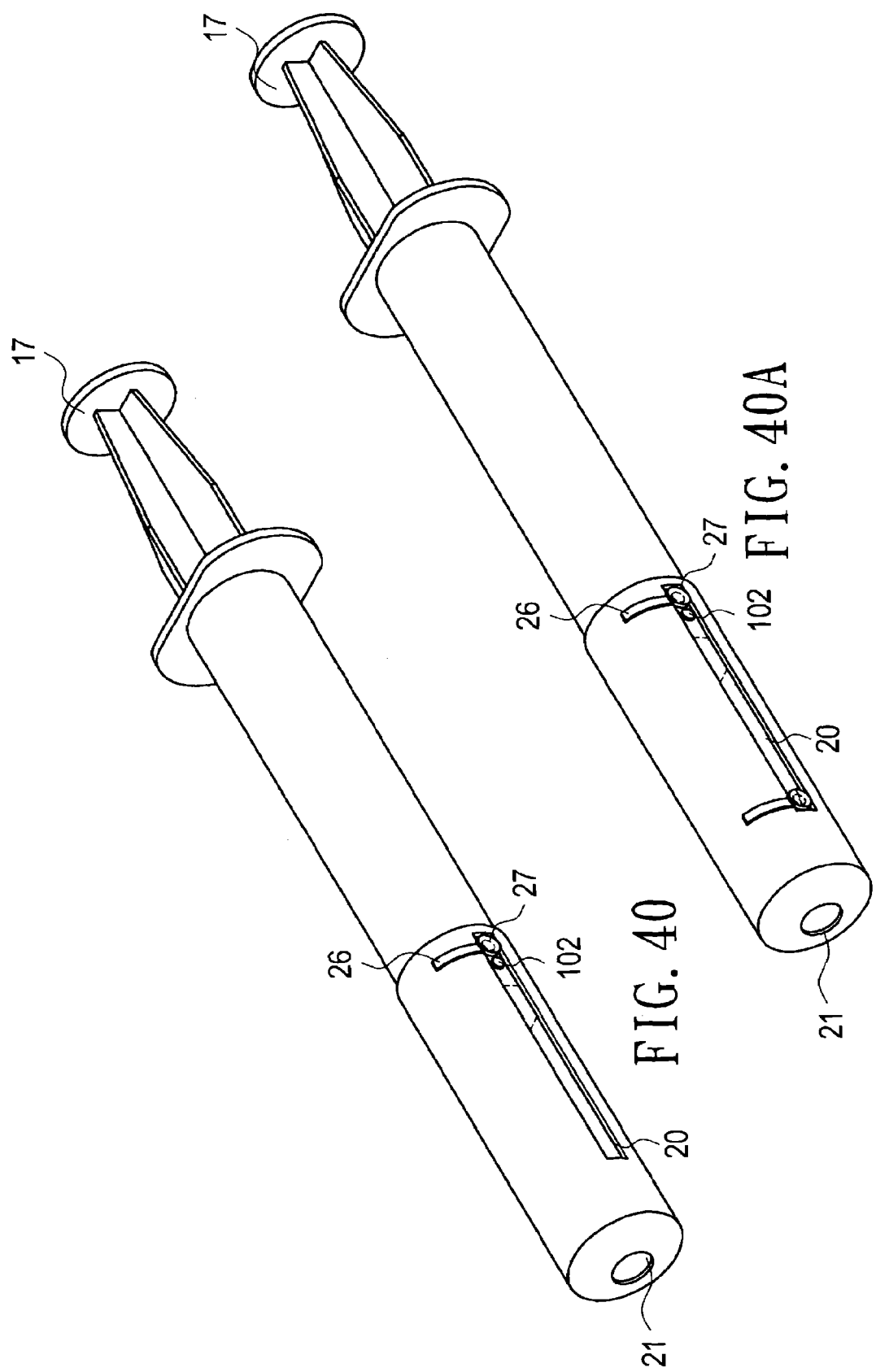

STERILIZED SAFETY SYRINGE

BACKGROUND OF THE INVENTION

1. Field of the Invention

The present invention relates to a sterilized safety syringe, and more particularly, to a sterilized safety syringe which can perfectly protect the medical staff from being injured and contaminated by the injection needle inadvertently when performing injection.

2. Description of the Prior Art

A conventional medical syringe for injecting the drug solution into, or drawing the body fluid such as blood from the patient body is essentially composed of a syringe and an injection needle connected at its front end, and a tubular piston rod with a plunger telescopically slid in the syringe so as to infuse the drug solution into the patient body during its downward compression stroke, or draw the body fluid such as blood from the patient body into the syringe during its upward suction stroke. Before beginning the operation, a rubber band is used to bind around the portion immediately above the spot where the needle is to be applied in case the wrist or the upper leg is selected for injection, and a sterilized swab is used to clean up the pinpoint. After finishing the injection, another sterilized swab is used to tenderly press on the pinpoint so as to avoid follow flow of the body fluid (blood) after the needle is separated away from the patient body. In such a traditional operation of injection. Medicall staffs are sometime inadvertently stung by the needle he is handling or contaminated by the residual body fluid flowing out from the syringe that might become a cause of infection to the medical personnel.

In view of this, in order to palliate the shortcomings inherent to the conventional technique described above, the present inventor has delved into this matter with long time efforts and has come to realization of the present invention.

SUMMARY OF THE INVENTION

It is an object of the present invention to provide a sterilized safety syringe which can perfectly protect the medical personnel from being injured by the needle or infected by the residual body fluid in the syringe.

It is another object of the present invention to provide a sterilized safety syringe capable of minimizing the probability of contamination to the medical staff to zero by its innovative and unique structure.

To achieve the aforementioned objects, the sterilized safety syringe of the present invention comprises: a syringe tube, a protective cover, a sterilizer, and an air compressor.

The syringe tube contains a cavity with a guide slot formed between its outer edge and the inner wall of the syringe tube. The syringe tube has a sealed rear end and several air conducting tube are communicated with its cavity and the guide slot respectively.

The protective cover has a drilled hole at its front end and is provided with more than one sliding plates at its rear end thereof, the rear end of each sliding plate is formed into an annular flange together with a check fitting.

The sterilizer has a sterilized cotton swab affixed to its main body and a pallet sealed with a film provided to the front end of its main body, while the rear end of its main body is formed into a plug.

The air compressor is connected with several air feeding pipes.

Each sliding plate of the protective cover is fitted into the guide slot of the syringe tube and is forcibly in close contact with the wall of the guide slot with its annular flange. The rear end plug of the sterilizer is to plug into the drilled hole of the protective cover. The air conducting pipes of the syringe are connected with corresponding air feeding pipes of the air compressor.

BRIEF DESCRIPTION OF THE DRAWINGS

The above objects and other advantages of the present invention will become lucid by describing in detail the preferred embodiments of the present invention with reference to the attached drawings in which:

FIG. 5 is a longitudinal cross sectional view in a first embodiment of the present invention;

FIG. 6 through FIG. 8 respectively is a longitudinal cross sectional view illustrating the operation principle in a first embodiment of the present invention;

FIG. 26 is a longitudinal cross sectional view in a sixteenth embodiment of the present invention;

FIG. 27 is a longitudinal cross sectional view in a seventeenth embodiment of the present invention;

FIG. 30 is a longitudinal cross sectional view in a twentieth embodiment of the present invention;

FIG. 31 is a longitudinal cross sectional view in a 21th embodiment of the present invention;

FIG. 32 is a longitudinal cross sectional view in a 22th embodiment of the present invention;

FIG. 33 is a longitudinal cross sectional view in a 23th embodiment of the present invention;

FIG. 34 is a longitudinal cross sectional view in a 24$^{th}$ embodiment of the present invention;

FIG. 35 is a longitudinal cross sectional view in a 25$^{th}$ embodiment of the present invention;

FIG. 40 is a three dimensional perspective view in a 30$^{th}$ embodiment of the present invention;

FIG. 40A is a three dimensional perspective view of an alternative embodiment of FIG. 40.

DETAILED DESCRIPTION OF THE PREFERRED EMBODIMENT

Figure 1:
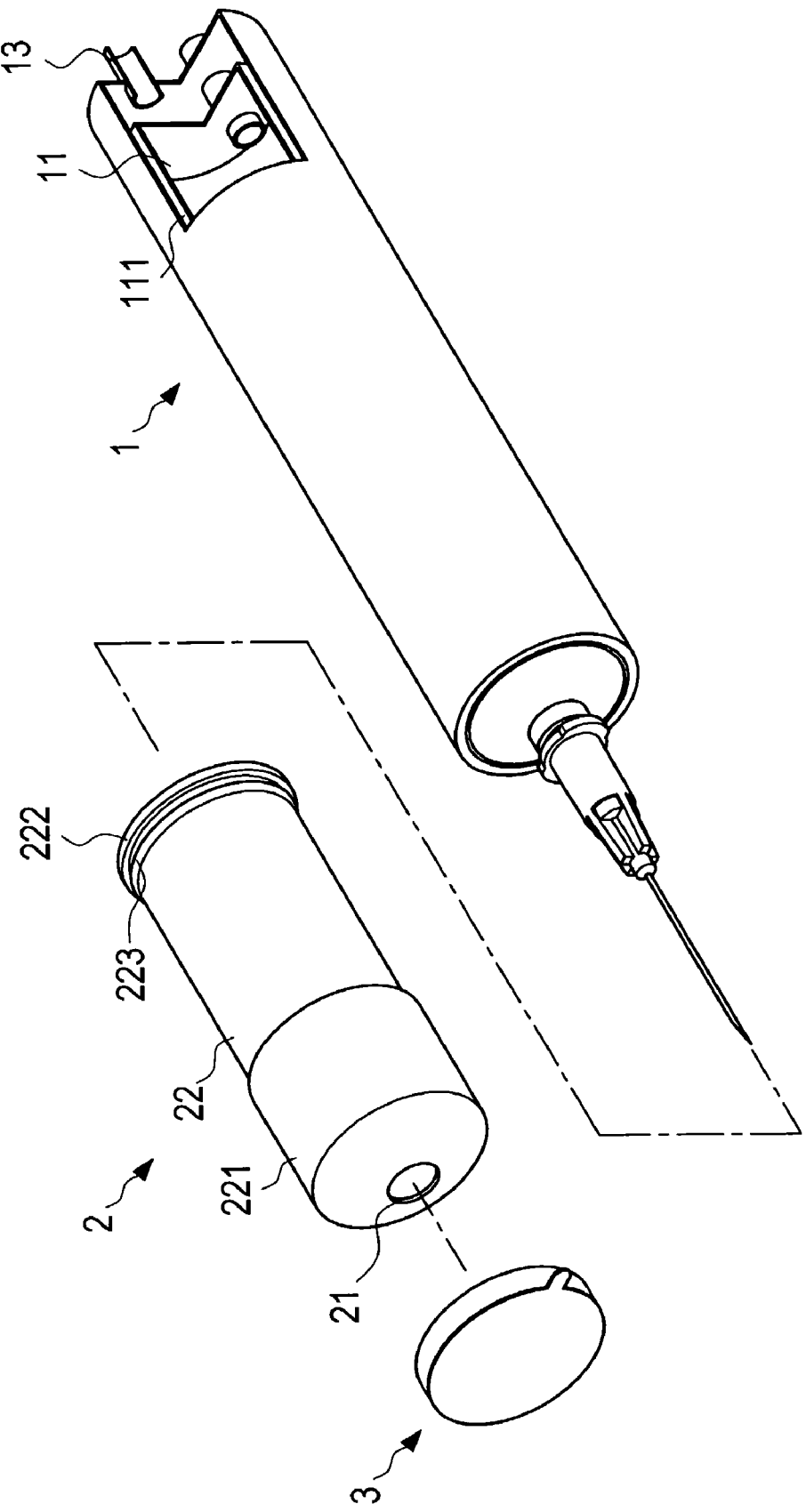
FIG. 1 is a three dimensional exploded view of the present invention.
Figure 2:
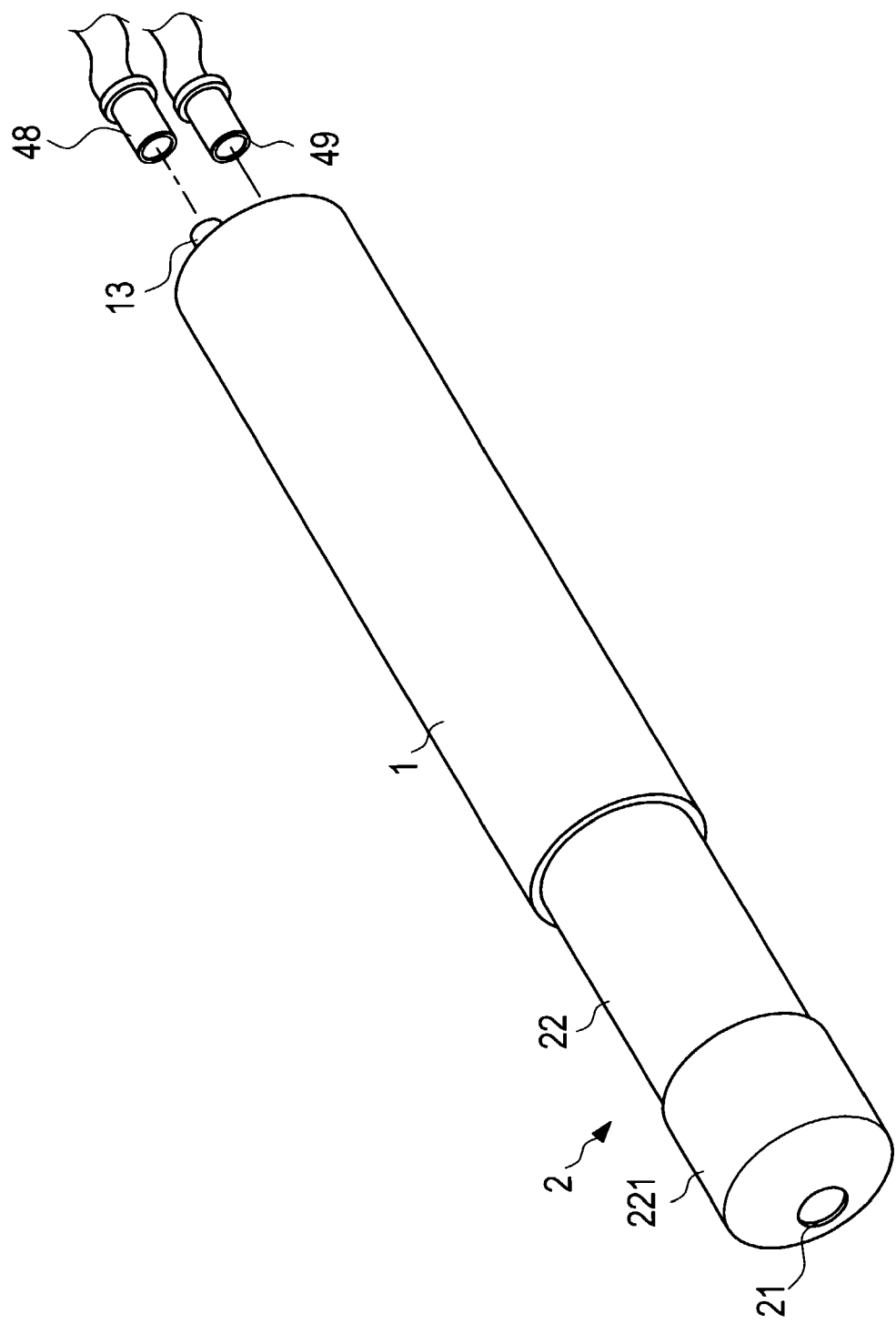
FIG. 2 is a three dimensional assembly view of the present invention.

Referring to FIGS. 1, 2, 3, 4, 5, and 9, in the first embodiment, the sterilized safety syringe of the present invention essentially comprises a syringe tube 1, protective cover 2, a sterilizer 3, and an air compressor 4.

The syringe tube 1 contains a cavity 11 with a guide slot 111 formed between the outer surface and the inner wall of the syringe tube 1. The guide slot 111 passes through the front wall surface of the syringe tube 1, and has a Protrusion 112 at its front end. A plunger 12 is provided in the cavity 11 and is closely in contact with the inner wall surface of the cavity 11. The rear end of the syringe tube 1 is in a sealed state where its cavity 11 and the guide slot 111 are communicated with a plurality of air conducting pipes 13 of said air compressor via an air conducting pipe 13;

The protective cover 2 has a drilled hole 21 at its front end and is provided with more than one sliding plate 22 at its rear end thereof. Each of the sliding plates 22 is provided with a fixed part 221 at its front portion, and an annular flange 222 at its rear end. The annular flange 222 has a check fitting 223 formed at its front edge.

The sterilizer 3 (see FIG. 5) has a pallet 32 formed at the front end of its main body 31, and a sterilized cotton swab 33 is affixed to the pallet 32. A film 34 formed at the front end of the main body 31 seals the pallet 32, while the rear end of the main body 31 is formed into a plug 35. Meanwhile, both the main body 31 and the plug 35 are formed of a soft rubber or plastic substance.

The air compressor 4 (see FIG. 3) is connected with a display terminal 41, an alarm 42, a controller 43, an encoder 44, a flow meter 45, a pressure sensor 46, and a plunger position detector 47, besides, several air feeding pipes 48 are connected to the air compressor 4.

Each sliding plate 22 pertaining to the protective cover 2 is fitted into the guide slot 111 of the syringe tube 1 and is forcibly in close contact with the wall of the guide slot 111 with its annular flange 222. The plug 35 formed at the rear end of the sterilizer 3 is plugged into the drilled hole 21 of the protective cover 2. The air conducting pipes 13 extended behind the syringe tube 1 are connected with corresponding air feeding pipes 48 of the air compressor 4.

For understanding how the sterilized safety syringe operate in the first embodiment of the present invention, the reference should be made to FIGS. 2, 3, 4, 5, 6, 7, 8, and 9. At the beginning, tear down the film 34 from the sterilizer 3, and wipe the spot of the patient skin to be injected with the sterilized cotton swab 33. Afterwards, extracting the air with the air compressor 4 through the air feeding pipes 48 which are communicated with the guide slot 111 via air conducting pipes 13 so as to create a negative pressure in the guide slot 111 thereby pulling the protective cover 2 backwards, and pushing the needle attached to the syringe tube 1 to stick into the patient skin via the sterilizer 3. At this moment, by a contact pressure created by the fixed part 221 clogging in the guide slot 111 and being halted at its outer edge by the protrusion 112 formed at the front end of the guide slot 111, the protective cover 2 is fixed behind the syringe tube 1. Then by suctioning or filling the air with the air compressor 4 via air feeding pipes 48, the operation of the syringe to infuse the drug into the patient body, or draw the body fluid therefrom can be performed. After the foregoing operation is finished, the air is fed via the air feeding tubes 48 with the air compressor 4, a positive pressure is created in the guide slot 111 so as to push the protective cover 2 forward until the sterilizer 3 located ahead of the protective cover 2 contacts the patient skin so that the needle may be pulled out of the patient body. During the aforesaid operation, the air compressor 4 continues to supply air to the guide slot 111 until the check fittings 223 of the protective cover 2 emerged out of the protrusion 112 at the front end of the guide slot 111 and halt the syringe tube 1 at its front end such that the protective cover 2 is also fixed in front of the syringe tube 1 and the needle is enclosed in the protective cover 2. Note that in this condition, the protective cover 2 is unable to retract backwards since its check fitting 223 has been hindered at the front edge of the syringe tube 1 such that reuse of the apparatus is prevented.

Figure 3:
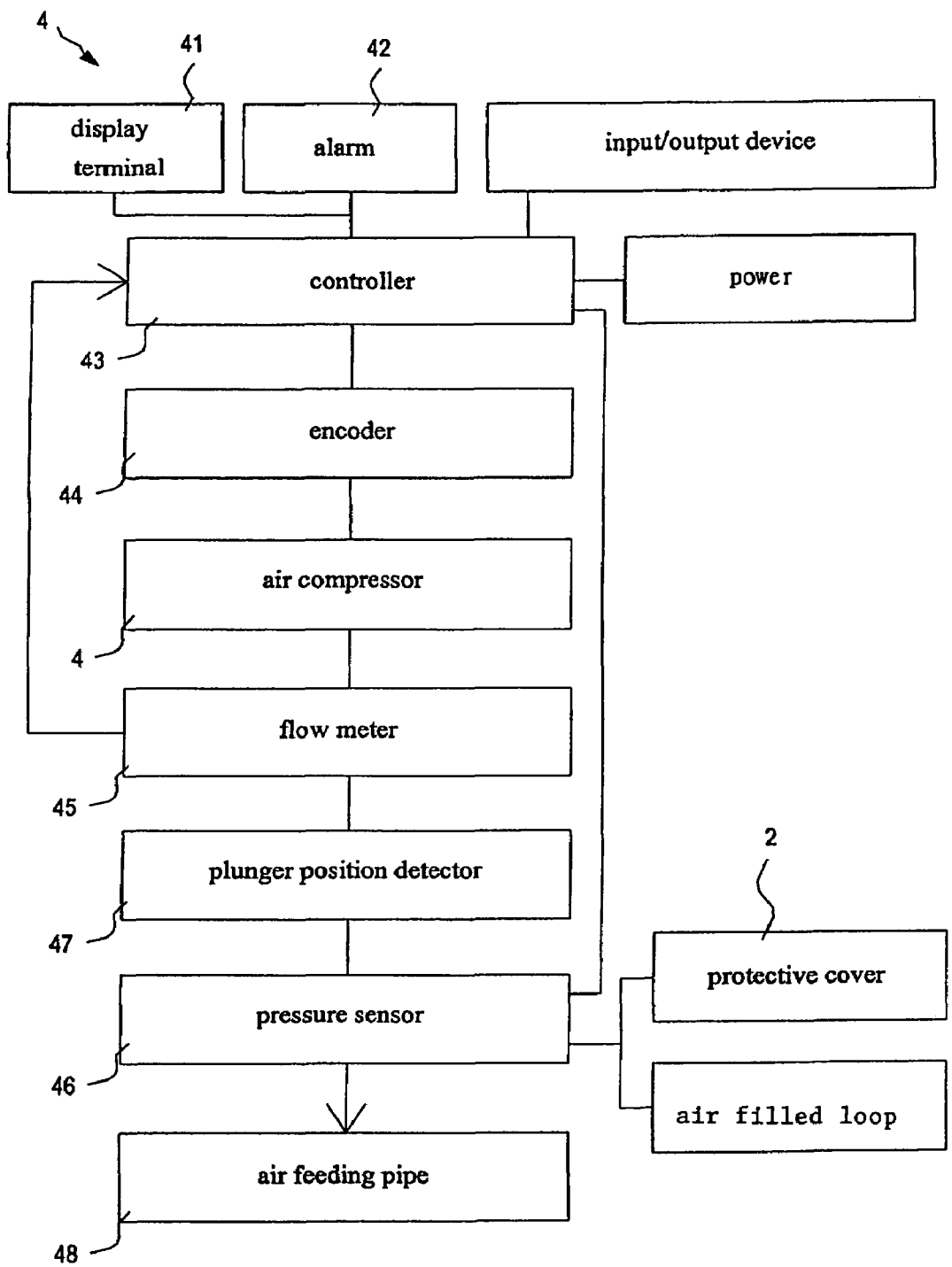
FIG. 3 is a block diagram illustrating the layout of the air compressor and its related accessories according to the present invention.
Figure 4:
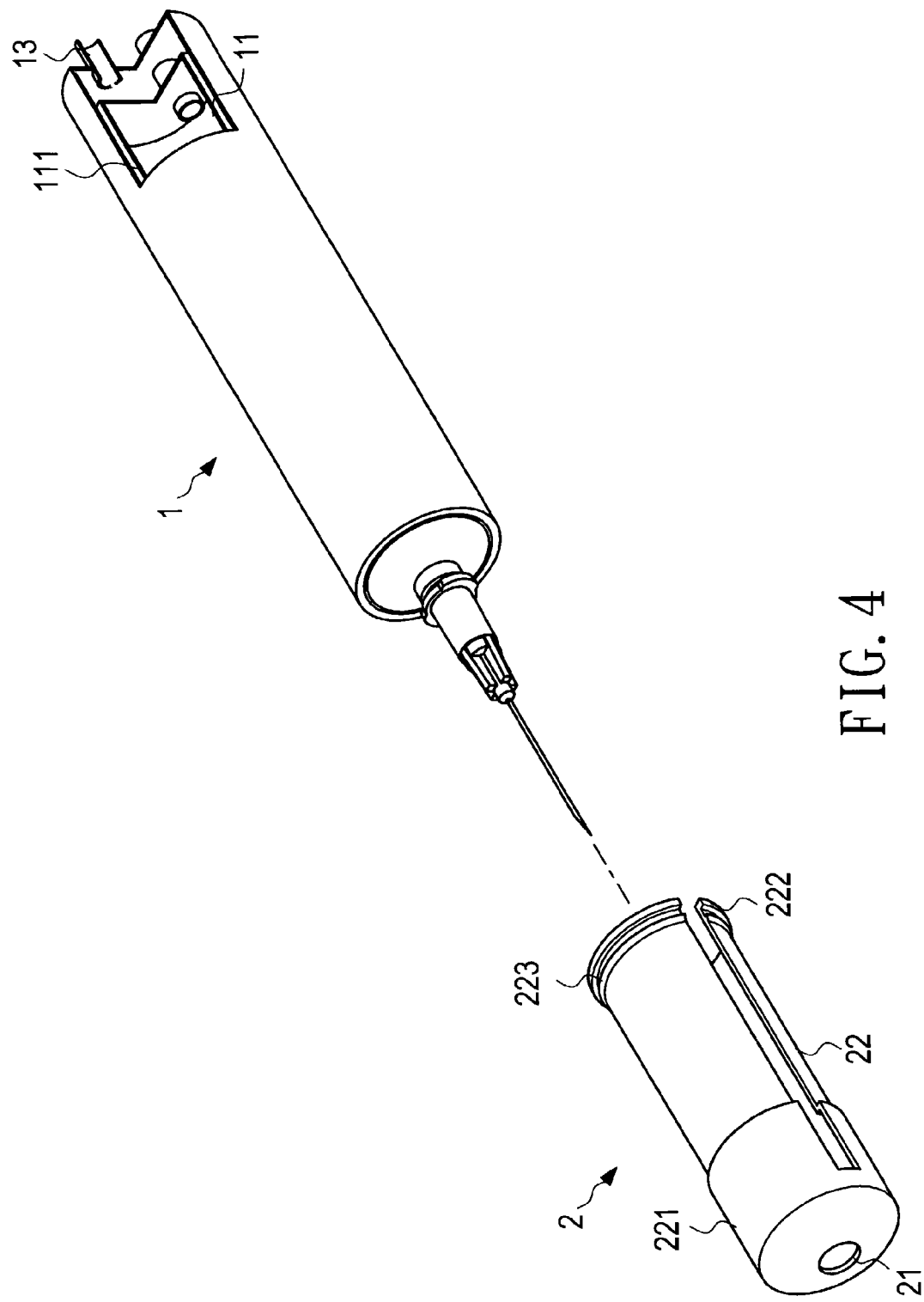
FIG. 4 is a three dimensional exploded view in a first embodiment of the present invention.
Figure 7:
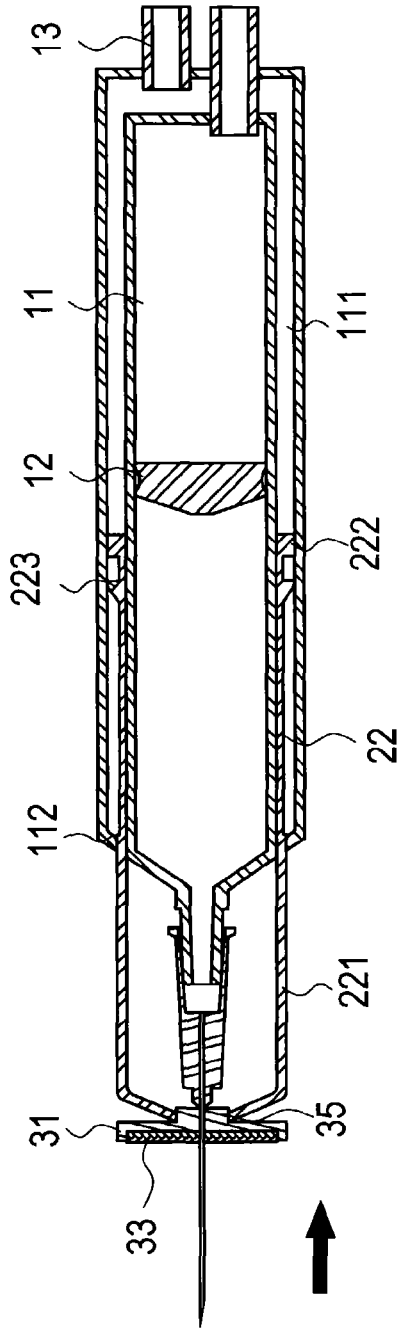
Figure 8:
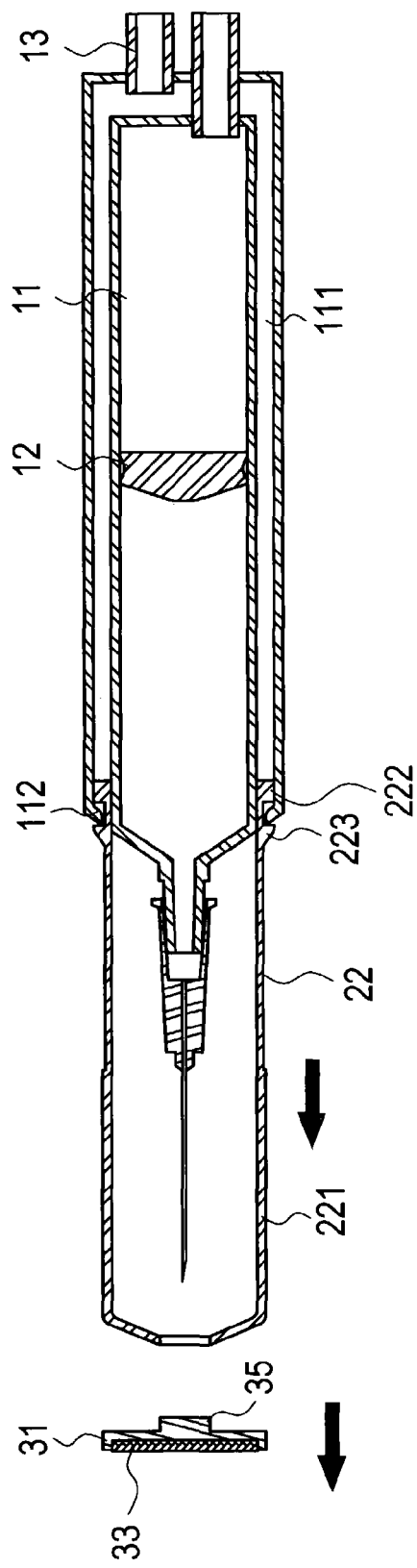

Referring to FIG. 1 together with FIG. 3, the air compressor 4 is provided with the display terminal 41 and the alarm 42. After finishing the operation, or in case the clogging of the needle or leakage of the content occurs, the alarm 42 will be actuated to caution the medical staffs. The plunger position detector 47 is for detecting the location of the plunger 12 in the syringe tube 1 so as to set the plunger 12 at an appropriate position by operating the air compressor 4 to push or pull the plunger 12 before beginning the operation. Besides the time required for infusing or extract may be estimated according to the location of the plunger. The adjustment of operation speed, e.g. control of time and quantity may be carried out by combination utilization of the controller 43, the encoder 44, and the flow meter 45. Moreover, the pressure sensor 46 provided for the air compressor 4 can detect the air leakage in the cavity 11 by monitoring the variation of pressure in the cavity 11 when supplying the compressed air into the cavity so as to perceive possible clogging or leakage. The pressure sensor 46 may be connected with the main body 31 of the sterilizer 3 to press the main body 31 on the patient skin where corresponding to the spot artery passes in case of extracting blood, a particular response is detected by the pressure sensor 46 should the pressed spot is exact. An input/output device of the air compressor 4 can be connected with PDA or a cellular phone. Alternatively, the air compressor 4 can be replaced with a liquid pressure pump. An air filled doughnut can be connected to the air compressor 4 with an air feeding pipe 48 to replace the conventional rubber band bound above the injection point by expanding the air filled doughnut with air supplied from the air compressor 4. The air filled doughnut also can be connected to the pressure sensor 46 to count the pulse rate of the patient. With this the medical staff is able to stop operation of injection should the patient pulse rate is too fast so as to release the patient's uneven feeling. The piston position detector 47 is for detecting the position of the plunger 12 in the injection syringe 1.

Referring to FIGS. 2, 3, 9, 10 and 11, in the present invention, the main body 31 and plug 35 of the sterilizer 3 are both made of a soft rubber substance or a soft plastic substance. Because of the specific elastic property of the above said materials, the pinhole bored through the main body 31 and the plug 35 after withdrawal of the needle for completion of injection will immediately readhered and disappeared such that the contamination to the medical staff by follow flow of the residual drug or body fluid from the needle can be avoided. Alternatively, the sterilized cotton swab 33 may be replaced with an alcohol swab or the like, the front end of the main body 31 of the sterilizer 3 can do without the film 34 to seal the cotton swab 33, but instead, by forming more than one protuberances 312 on the rim of the main body 31, and an annular ring 37 provided ahead of a container 39 is used to fit on the rim of the main body 31. There are several breaches 371 formed at the positions corresponding to the protuberances 312, and a protruded tip 372 is formed ahead of the opening of each breach 371 to catch the corresponding protuberance 312 so as to fix the container 39 around the rim of the main body 31. Besides, a pallet 32 with a sterilized cotton swab 33 is provided in front of the container 39, and the pallet 32 is sealed with a film 34. Before operation of the present invention, tear down the film 34 from the container 39, and rub the patient skin with the sterilized cotton swab 33, after that take down the container 39 from the main body 31. After finishing the operation, press on the injection pinpoint of the patient with the cotton swab 33 to stop blooding. Alternatively, a doping cotton swab 341 intercalated between front and rear sealing films which are adhered each other can be used to dope the patient injection point before injection takes place. Meanwhile, a knob 36 (see FIG. 10) may be provided at the rear part of the main body 31 of the sterilizer 3 for the convenience of handling by the medical staff or the patient. Besides, a sensor paper 49 (see FIG. 2) may be installed at the joint portion between the air feeding pipe 48 and the air conducting pipe 13 to detect the contaminated compression air coming from the air compressor 4 by varying the color thereof so as to urge the medical staff it is the time to clean up the air compressor 4 thereby preventing infectant contamination to the injection drug and the body fluid.

Figure 12:
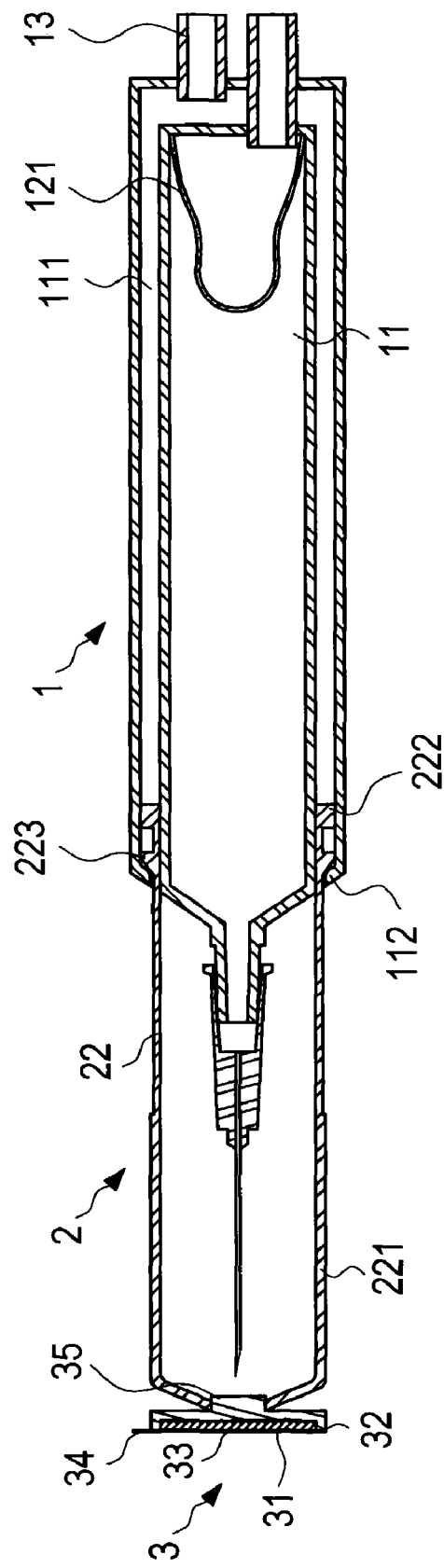
FIG. 12 is a longitudinal cross sectional view in a second embodiment of the present invention.
Figure 14:
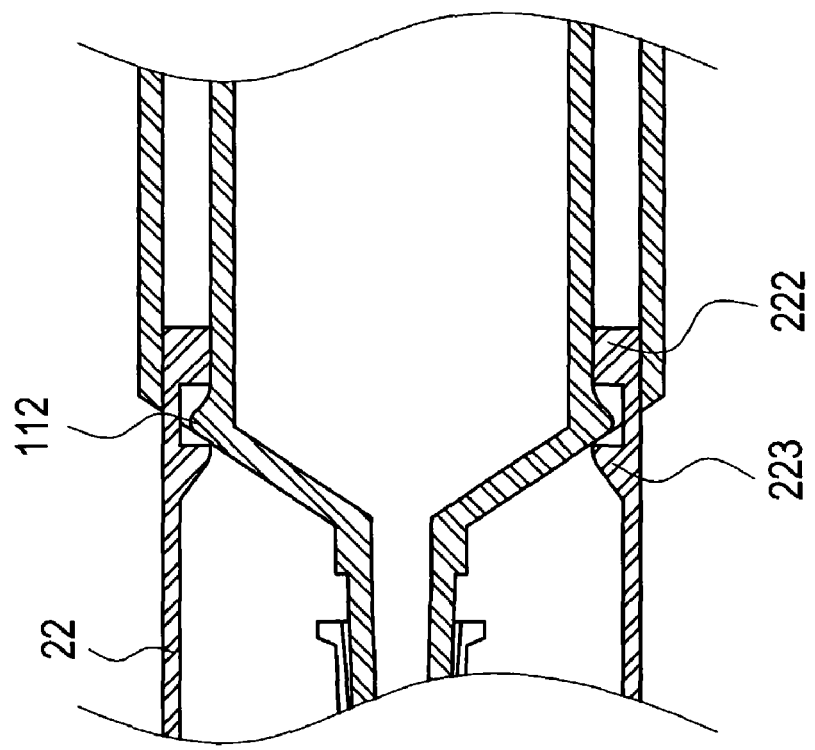
FIG. 14 is a fragmentary longitudinal cross sectional view in a fourth embodiment of the present invention.
Figure 13:
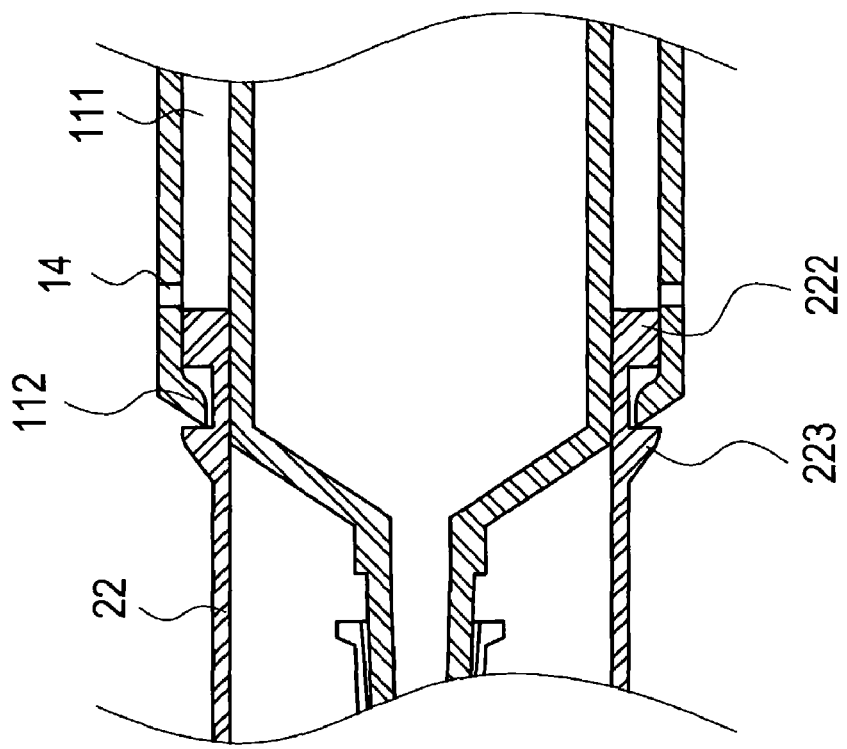
FIG. 13 is a fragmentary longitudinal cross sectional view in a third embodiment of the present invention.

In the second, third and fourth embodiments of the present invention shown in FIG. 12 though FIG. 14, the plunger 12 can be replaced with an air filled bag 121 made of a material similar to that of a balloon. Several air exhausting holes 14 communicating with the guide slot 111 are formed on the front outer edge of the syringe tube 1. After being finished operation, the compressed air filled in the guide slot 111 is discharged from the air exhausting holes 14. In this manner the repeated use of the syringe is prohibited since no more air remains in the guide slot 111 to create negative pressure to attract the protective cover 2 backward. Meanwhile, the annular flange 222 and the check fittings 223 for the protective cover 2 may be formed facing inner side of the sliding plate 22 as shown in FIG. 14.

Figure 15:
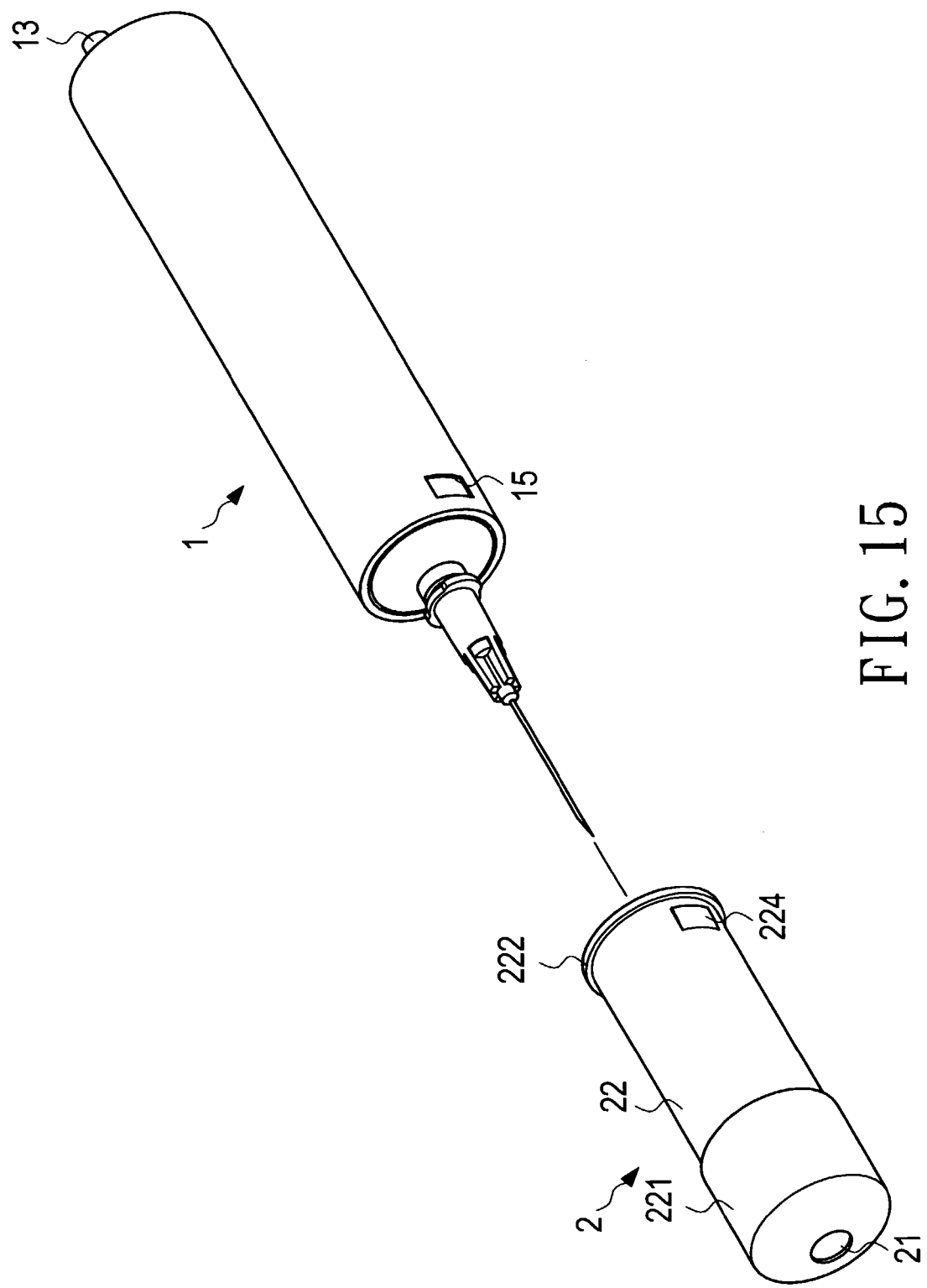
FIG. 15 is a three dimensional exploded view in a fifth embodiment of the present invention.
Figure 16:
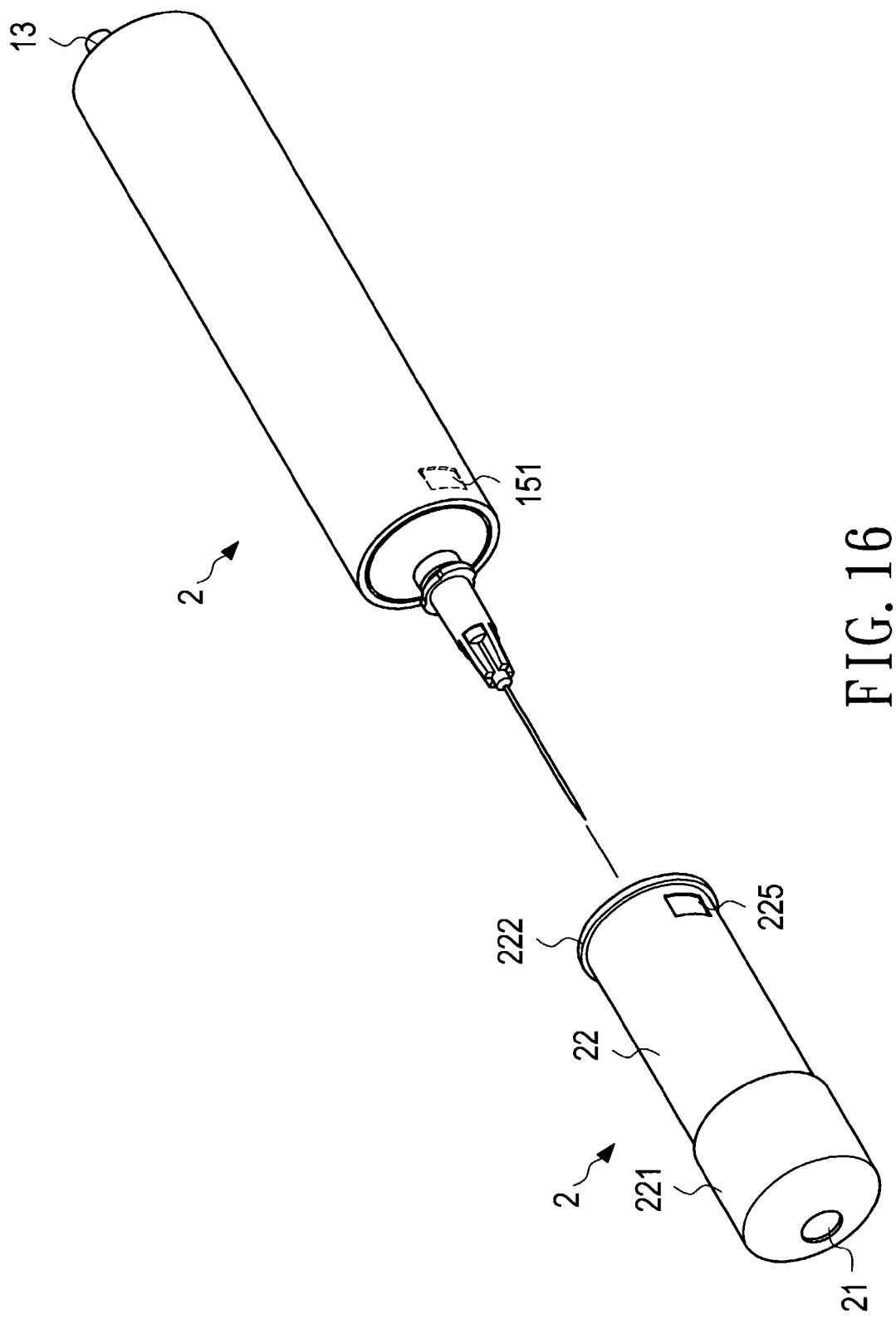
FIG. 16 is a three dimensional exploded view in a sixth embodiment of the present invention.

In the fifth and sixth embodiments of the present invention show in FIGS. 15 and 16, the check fitting 223 for the protective cover 2 may be saved, and instead, several protuberances 224 are formed on the rear outer surface of the protective cover 2, and several apertures 15 which corresponding in number and position to the protuberances 224 are opened on the front outer surface of the syringe tube 1. After being finished operation of the present invention either infusing drugs or extracting body fluid, the air compressor 4 continues on pumping air to the guide slot 111 so as to engage the protuberances 224 of the protective cover 2 with the corresponding apertures 15 of the syringe tube 1 thereby the protective cover 2 is fixed to the front edge of the syringe tube 1 (see FIG. 15). Alternatively, the apertures 225 are formed on the outer rear surface of the protective cover 2, and the protuberance 151 which corresponding in number and position are formed at the front end of the guide slot 111 (see FIG. 16). By so, after being finished operation of the present invention either injecting drugs or extracting body fluid, the air compressor 4 continues on pumping air to the guide slot 111 so as to engage the protuberances 151 of the syringe tube 1 with the corresponding apertures 225 of the protective covers 2 thereby fixing the protective cover 2 to the front edge of the syringe tube 1 as shown in FIG. 16.

Figure 17:
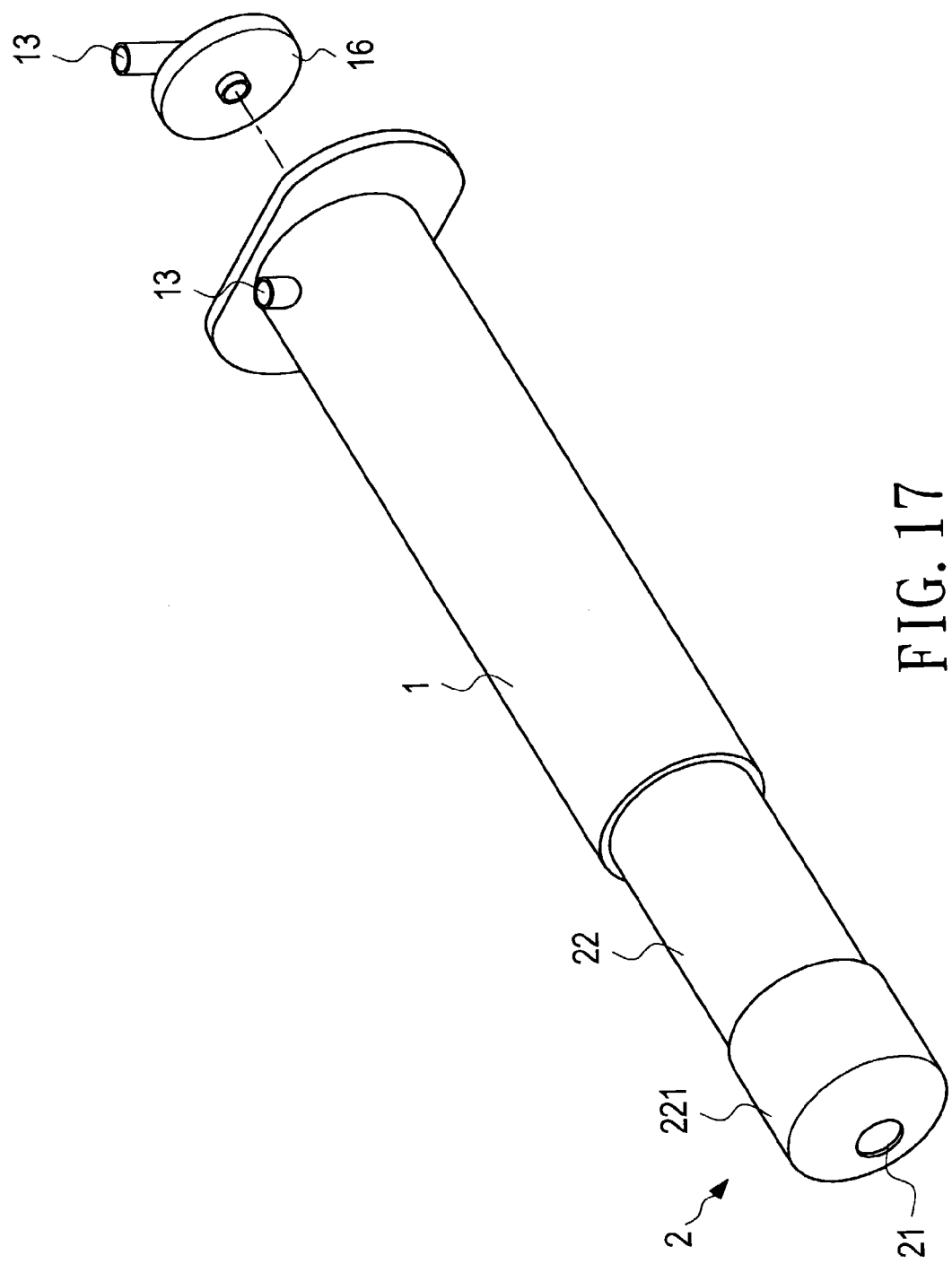
FIG. 17 is a three dimensional exploded view in a seventh embodiment of the present invention.
Figure 18:
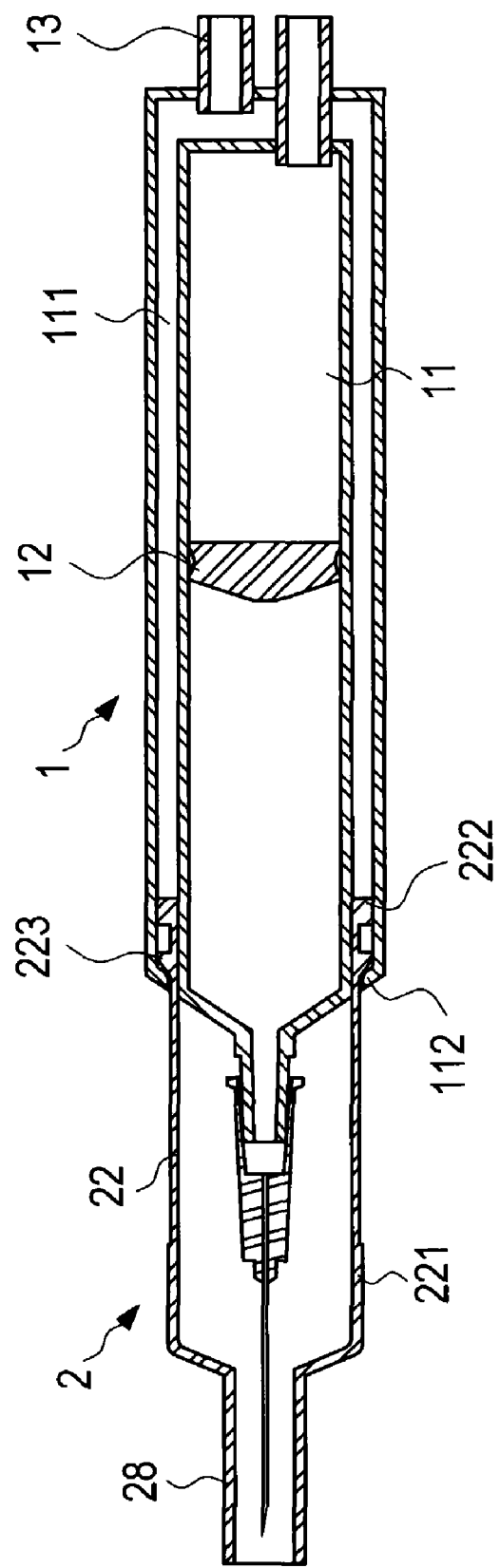
FIG. 18 is a longitudinal cross sectional view in a eight embodiment of the present invention.
Figure 19:
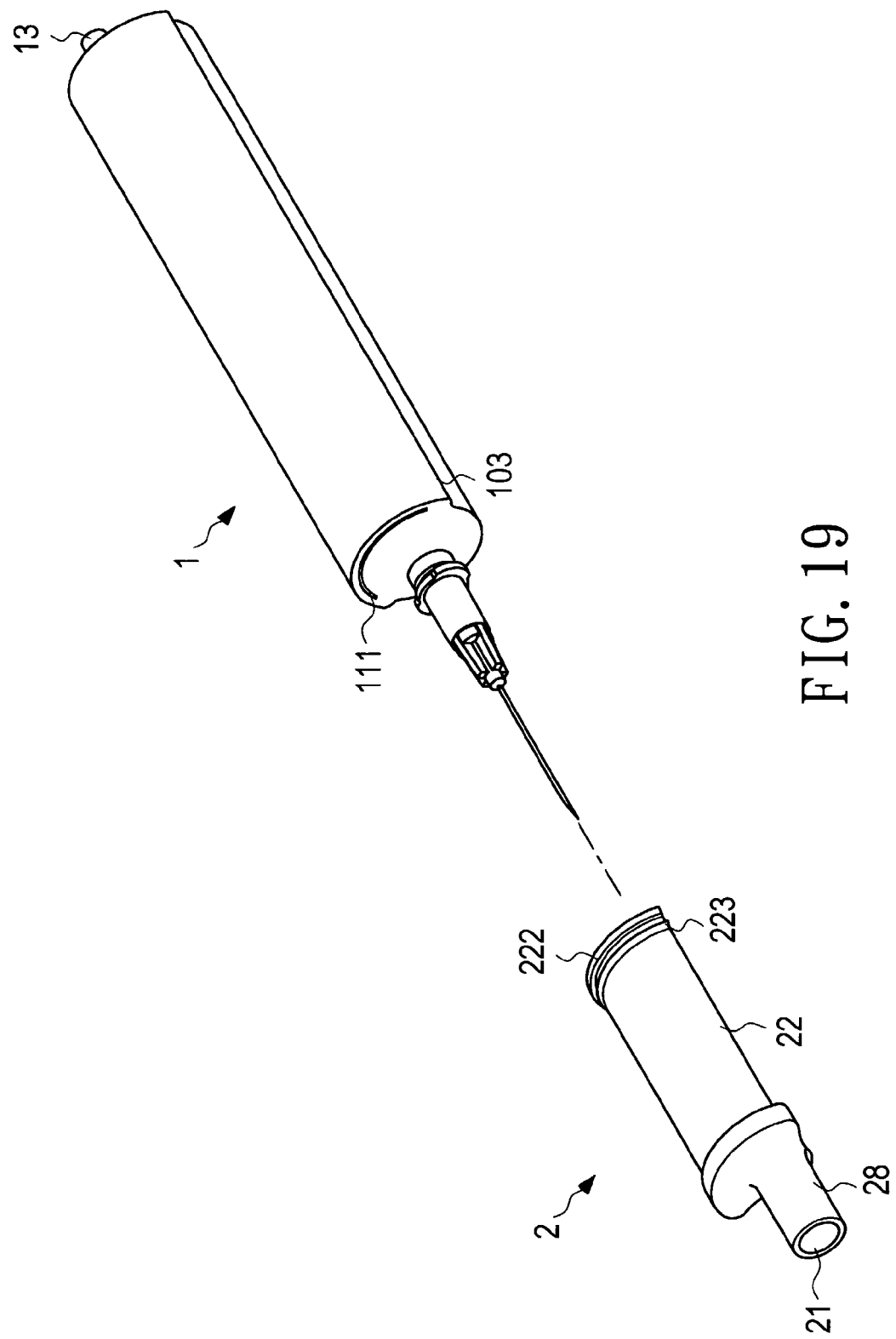
FIG. 19 is a three dimensional exploded view in a ninth embodiment of the present invention.

In the seventh, eight, and ninth embodiments of the present invention shown in FIG. 17 through FIG. 19, the rear end of the syringe tube 1 is not sealed (see FIGS. 17, 18) and the air conducting pipe 13 is connected to the guide slot 111, and the plunger 16 with the other air conducting tube 13 connected to the cavity 11 is provided at the rear end of the syringe tube 1 as shown in FIG. 17. Besides, a protruded annular protector 28 affixed with a single sliding plate 22 to its rear end thereof is formed at the front end of the protective cover 2, and a sliding groove 103 corresponding to the single sliding plate 22 is formed along the outer surface of the cavity 11 of the syringe tube 1 for serving as a track for the singe plunger 22 as shown in FIG. 19.

Figure 20:
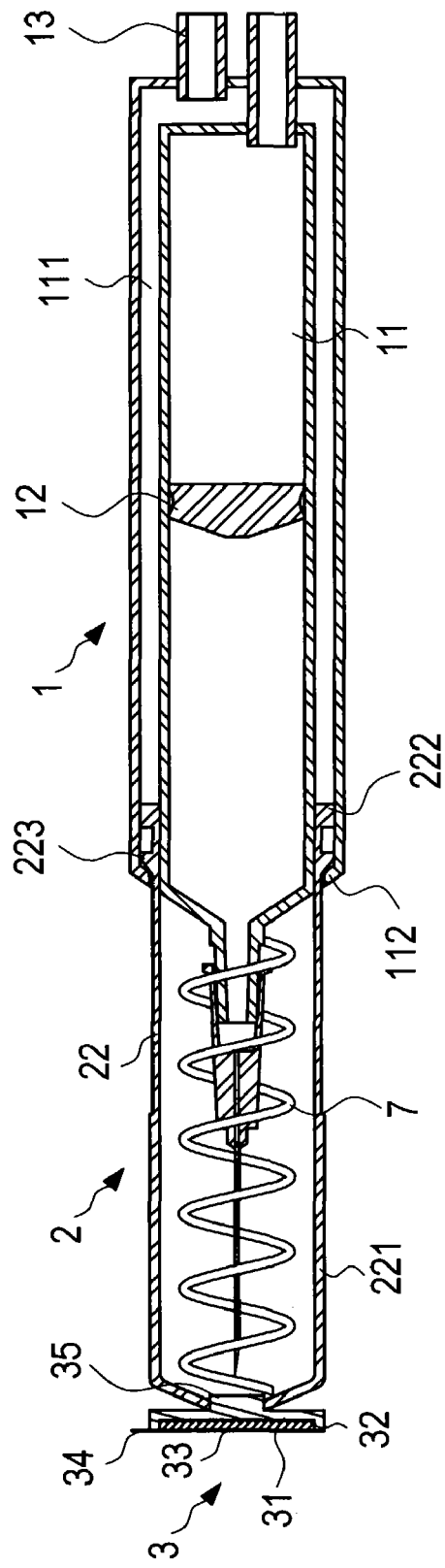
FIG. 20 is a longitudinal cross sectional view in a tenth embodiment of the present invention.
Figure 21:
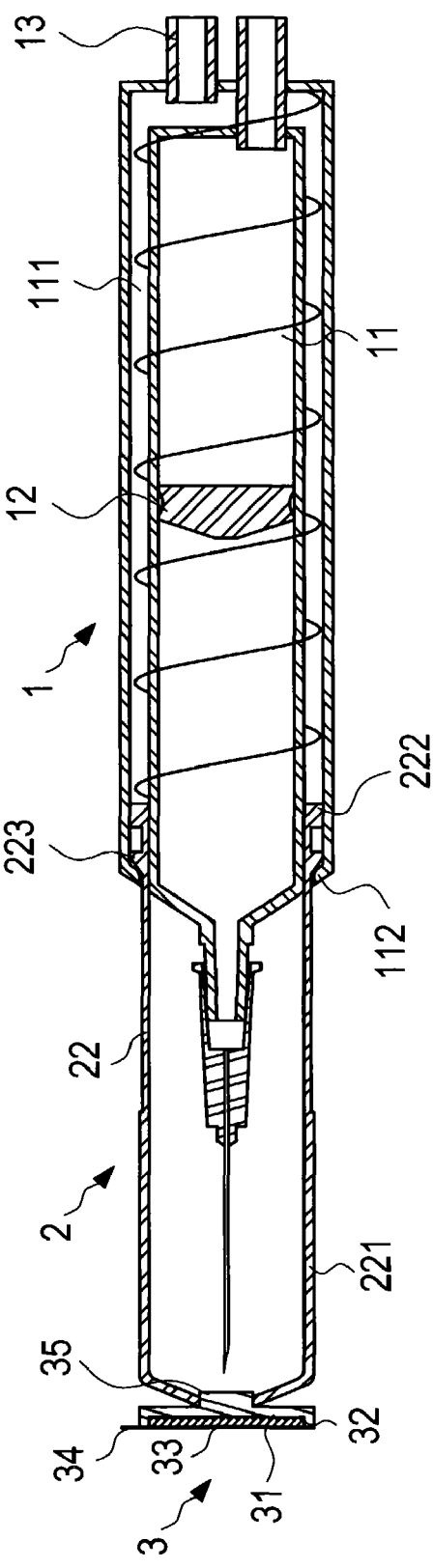
FIG. 21 is a longitudinal cross sectional view in a eleventh embodiment of the present invention.

In the tenth and eleventh embodiments of the present invention shown in FIGS. 20 and 21, in the protective cover 2, a coil spring 7 connected to the front tip of syringe tube 1 is provided as shown in FIG. 20. alternatively, the coil spring 7 is inlaid in the guide slot 111 of the syringe tube 1 and connected with the annular flange 222 at the rear end of the protective cover 2 as shown in FIG. 21. When operation of the injection takes place, the needle is stuck into the patient body by pressing the sterilizer thereon. At this moment, the coil spring 7 either in the protective cover 2 (see FIG. 20), or in the guide slot 111 (see FIG. 21) is compressed and then elongated by its own restoring force to push forward the protective cover 2 when the force applied on the patient is released at the moment injection is over. As a result, the check fitting 223 of the protective cover 2 slides out of the guide slot 111 and is halted by the front wall of the syringe tube 1 so that the protective cover 2 can not retract.

Besides, the spring 7 may be equipped at the rear end of the protective cover 2 so as to be jointed to the rear wall of the sliding groove 111.

Figure 22:
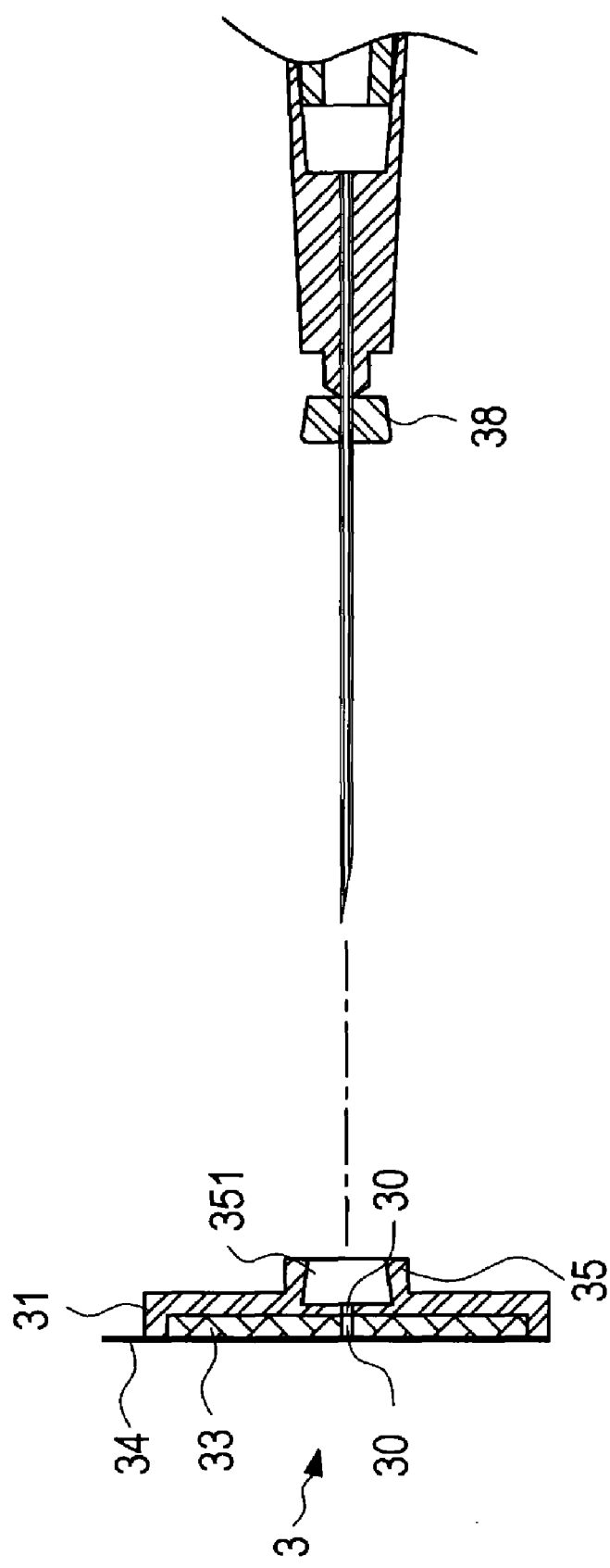
FIG. 22 is fragmentary longitudinal cross sectional view in a twelf embodiment of the present invention.

In the twelfth embodiment of the present invention shown in FIG. 22, a center drilled hole 30 is opened through the main body 31, and the sterilized cotton swab 33, and a confinement slot 351 is formed at the rear end of the plug 35. A cork gasket 38 made of an elastic rubber or plastic substance which is being inserted into the needle ahead of the syringe tube 1. In operating the present invention, the film 34 is at first torn off from the sterilizer 3, then the needle pokes through the main body 31 and sterilized cotton swab 33 and emerges out of the drilled hole 30 so as to bring the cork gasket 38 trapped in the confinement slot 351. After finishing the injection, the cork gasket 38 together with the sterilizer 3 are separated from the needle and the pinhole on the cork gasket 38 is automatically clogged by the inherent adhesiveness of its material thereby stopping follow flow of infusing drugs or body fluid which probably cause an infectant contamination.

Figure 23:
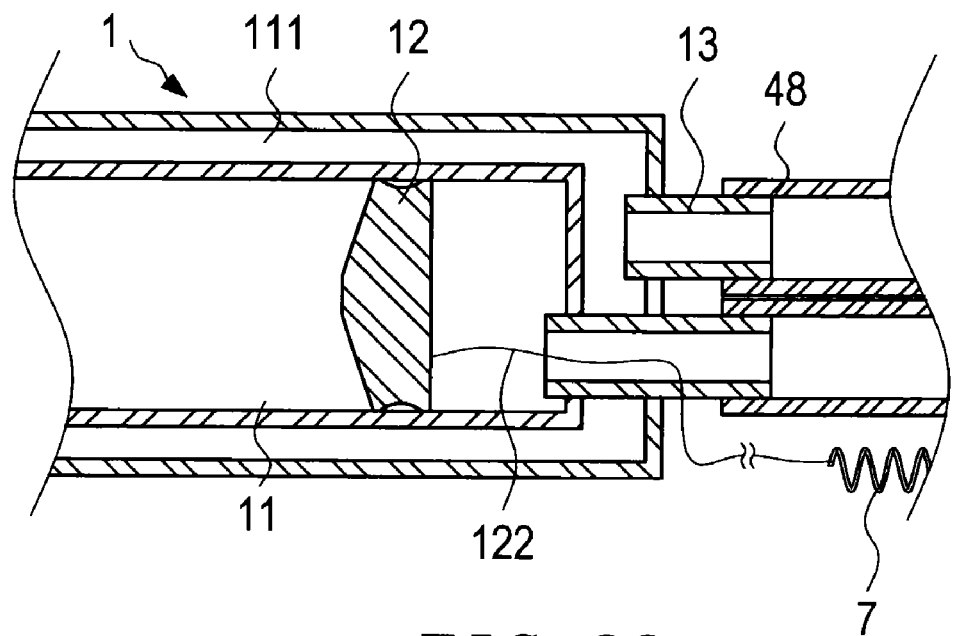
FIG. 23 is a fragmentary longitudinal cross sectional view in a thirteenth embodiment of the present invention.
Figure 24:
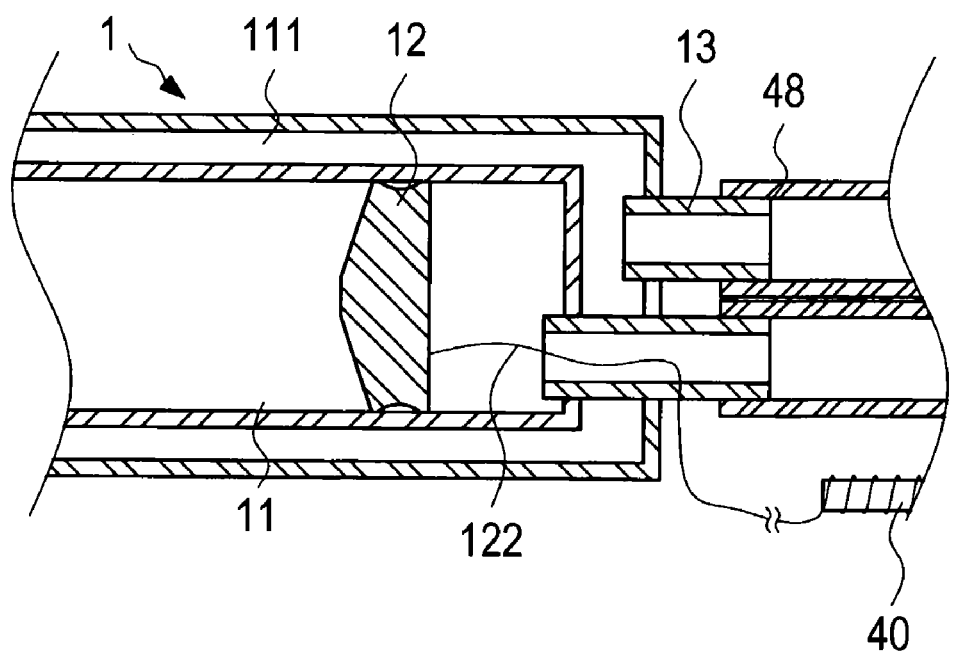
FIG. 24 is a fragmentary longitudinal cross sectional view in a fourteenth embodiment of the present invention.

In the 13th and 14th embodiment of the present invention shown in FIGS. 23 and 24, the coil spring 7 is installed on the air compressor 4, and is connected to the rear end of the plunger 12 with a metallic wire 122 at its front end. When the plunger reciprocates forwards and backwards, the coil spring 7 is elongated by the pulling force of the metallic wire 122 (in forwards motion), or retracted by its own restoring force (in backwards motion) thereby causing the air compressor 4 be aware of the position of the plunger 12 (see FIG. 23). On the other hand, an rotating shaft 40 is provided to the air compressor 4, the metallic wire 122 is wound around the shaft 40 and its front end is attached to the rear end of the plunger 12 so that the air compressor 4 is able to figure out the displacement of the plunger 12 by the number of turns of the metallic wire 122 wound on the shaft 40. Meanwhile, in the present invention, a frequency generator may be equipped with the compressor 4 to produce a resonant frequency to detect the amount of the displacement of the plunger 12 by the return signal therefrom.

Figure 9:
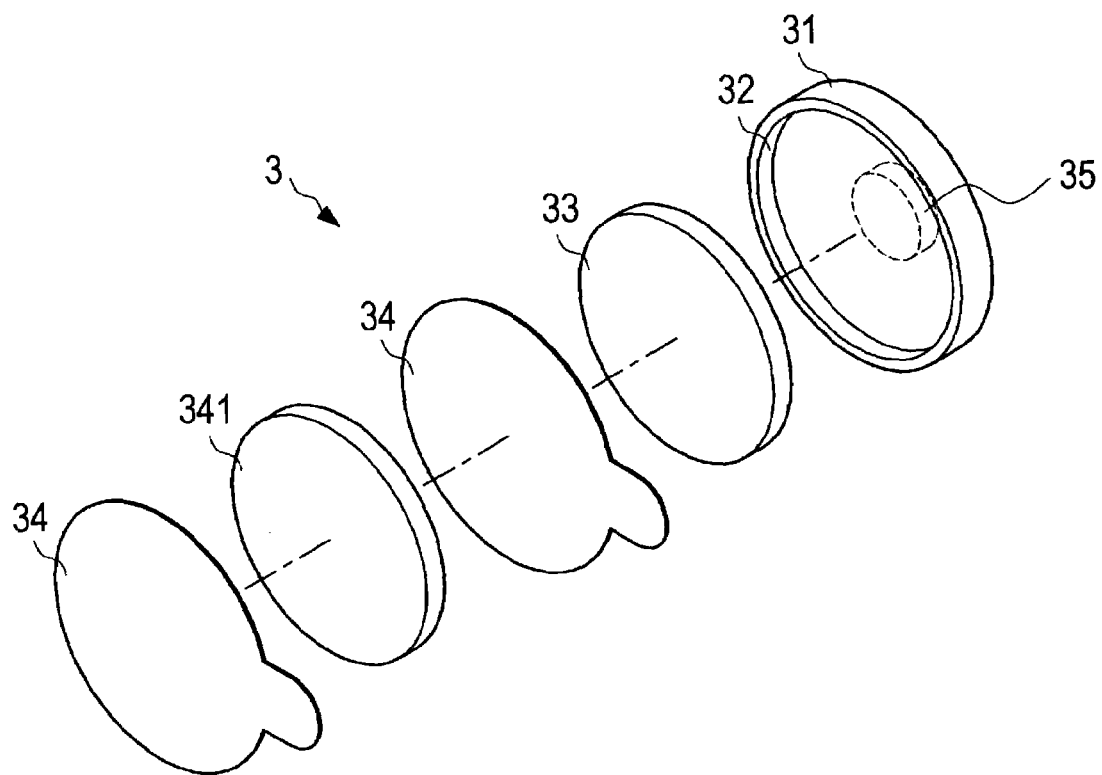
FIG. 9 is a three dimensional exploded view of the sterilizer.
Figure 10:
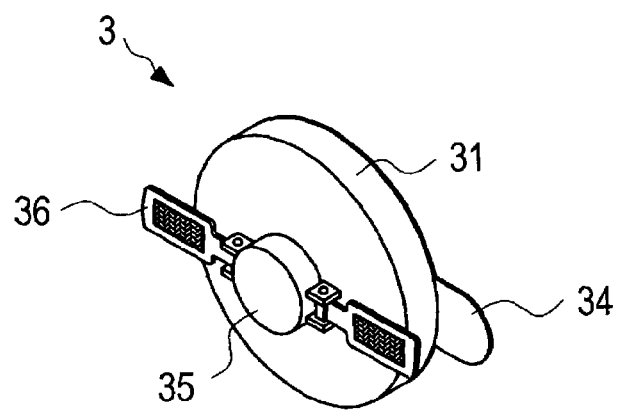
FIG. 10 is a three dimensional view of the sterilizer in a first embodiment.
Figure 11:
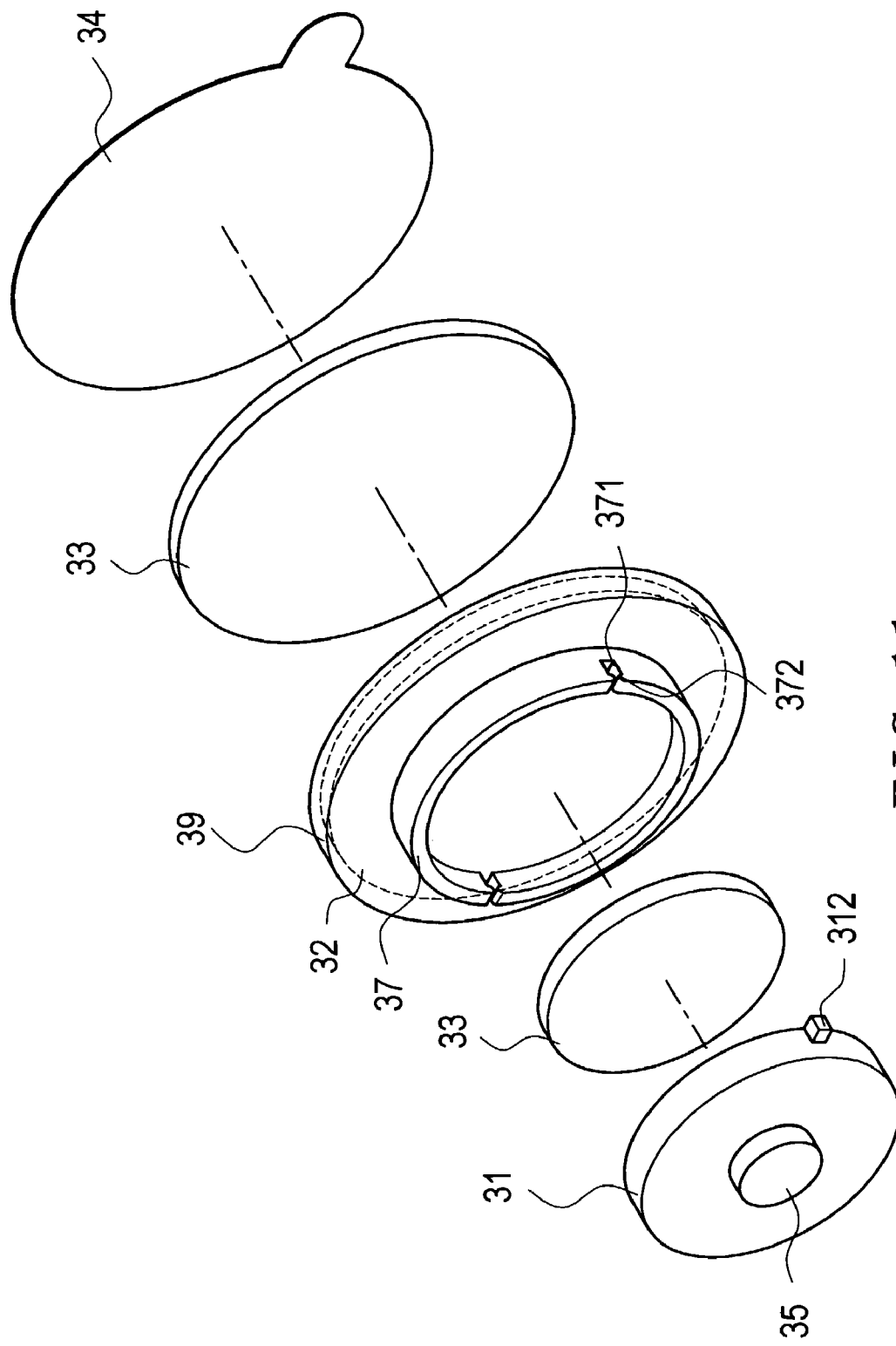
FIG. 11 is a three dimensional exploded view of the sterilizer is a second embodiment.
Figure 25:
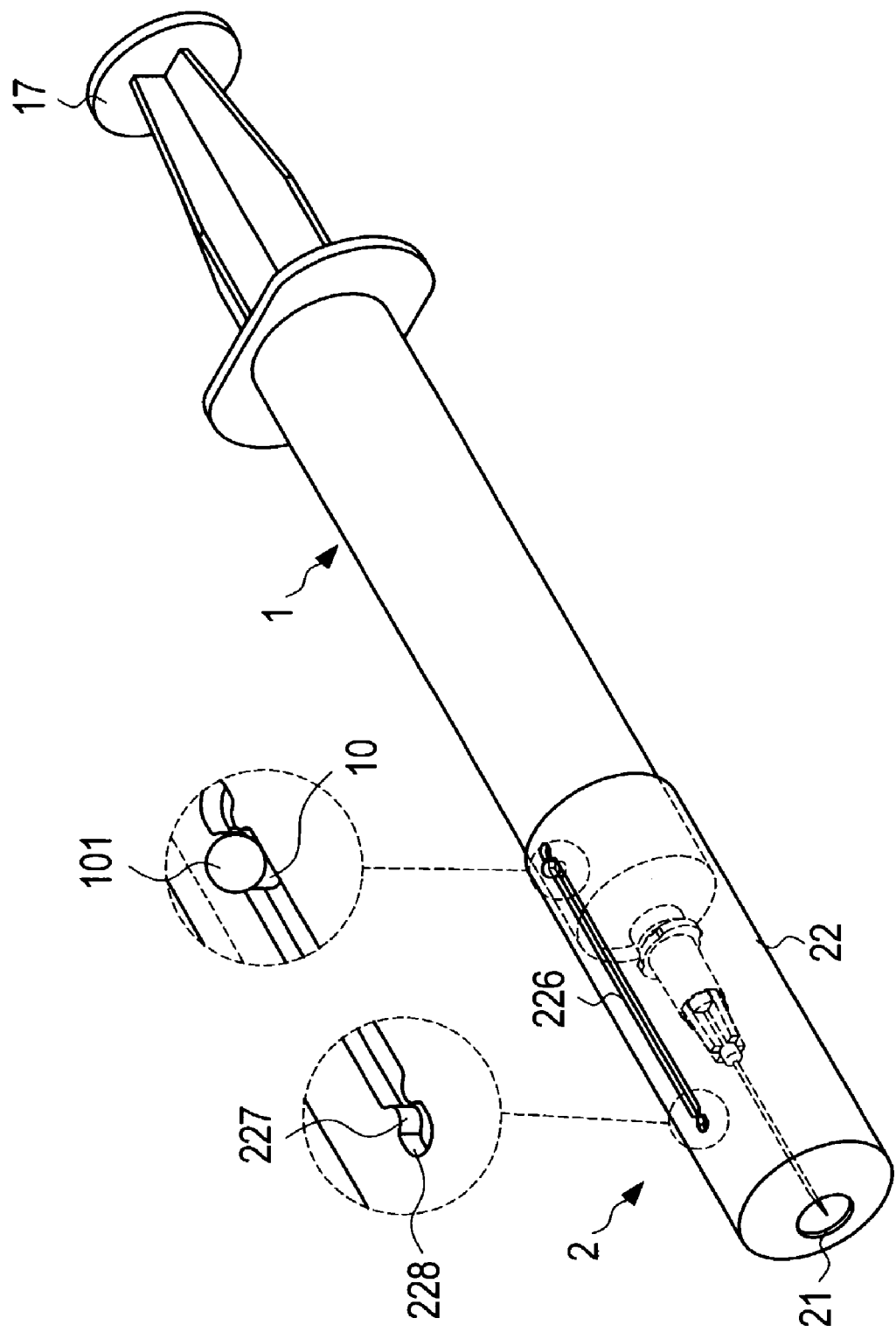
FIG. 25 is a three directional perspective view in a fifteenth embodiment of the present invention.

Referring to FIGS. 9 and 25, in the 15th embodiment of the present invention, the sterilized safety syringe essentially comprises a injection tube 1, protective cover 2, a sterilizer 3.

There are more than one guide rods 10 formed along the outer surface of the syringe tube 1 and each of the guide rods 10 has a round billet 101 on it. The syringe tube 1 is provided with a piston rod 17 whose front periphery is closely in contact with the inner wall of the syringe tube 1.

The protective cover 2 has a drilled hole 21 at its front end, and a sliding plate 22 at its rear end. Several sliding grooves 226 are formed along the sliding plate 22 at the positions corresponding to the guide rods 10 respectively. A damper 227 is provided near both front and rear ends of each sliding groove 226 respectively such that both ends of each sliding groove, 226 is formed into fixed terminals 228.

As shown in FIG. 9, the sterilizer 3 has a pallet 32 provided at the front end of its main body 31, and a sterilized cotton swab 33 is affixed to the pallet 32. A film 34 formed at the front end of the main body 31 seals the pallet 32, while the rear end of the main body 31 is formed into a plug 35.

The guide rod 10 is inserted into the sliding groove 226 of the protective cover 2, and the round billet 101 is clogged at the tip of the sliding groove 226. The plug 35 of the sterilizer 3 is plugged into the drilled hole 21 of the protective cover 2.

Referring to FIGS. 26 and 27, in the 16$^{th}$ and 17$^{th}$ embodiments of the present invention, a syringe tube 1 has a cavity 11 inside, and a guide slot 111 is formed between the outer surface of the cavity 11 and the inner wall surface of the tube 1, the guide slot 111 emerges out of the front wall of the tube 1. The protective cover 2 is provided with an elastic hasp mechanism 23 which including a spring strap 231, a supporting stud 232, and an actuator plate 223. The supporting stud 232 is in contact with the front portion of the actuator plate 233, and a stop block 234 is formed at the rear bottom portion of the actuator plate 233. More than two recesses 19 are formed on the outer surface of the syringe tube 1 in the position along the same lengthwise line with the stop block 234. A coil spring 7 installed in the protective cover 2 is fixed its one end to the front end of the tube 1. (see FIG. 26) Alternatively, the coil spring 7 is installed in the guide slot 111 spirally wound around the syringe tube 1 as shown in FIG. 27.

Figure 28:
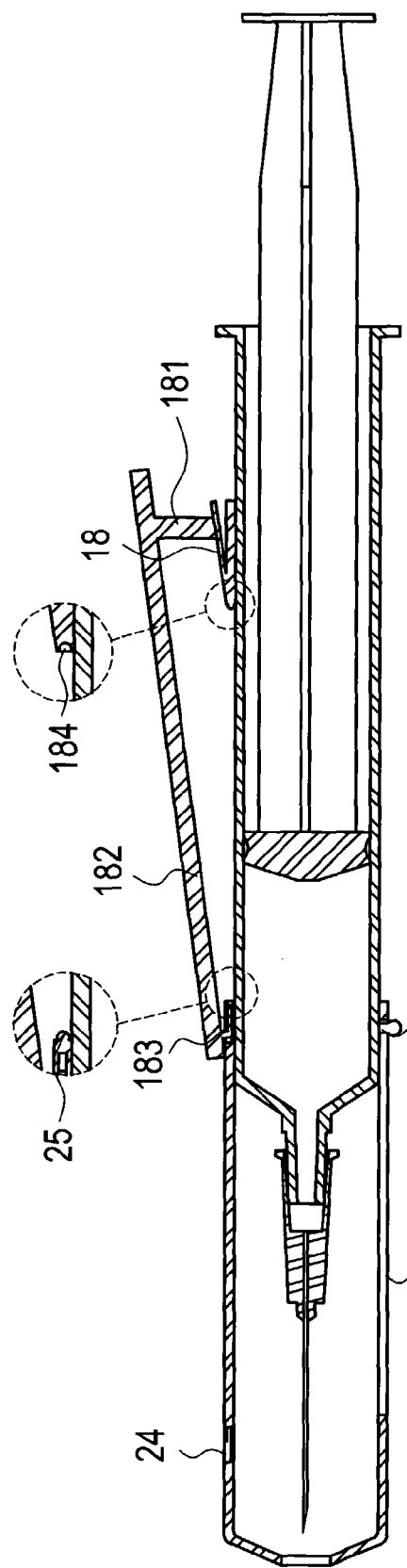
FIG. 28 is a longitudinal cross sectional view in a eighteenth embodiment of the present invention.
Figure 29:
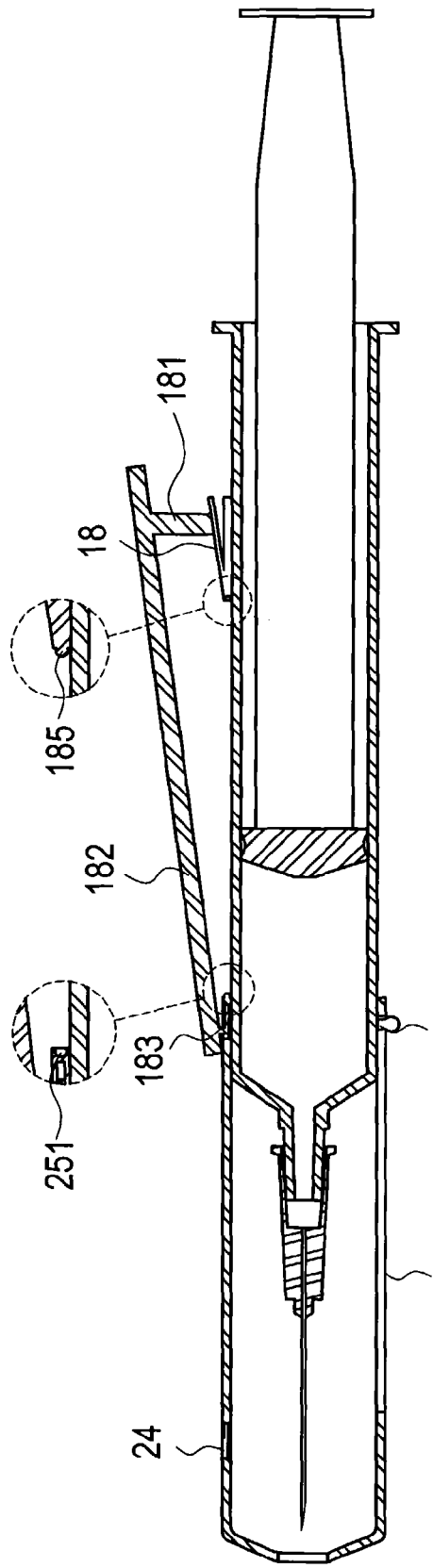
FIG. 29 is a longitudinal cross sectional view in a nineteenth embodiment of the present invention.

Referring to FIGS. 28 and 29, in the 18$^{th}$ and 19$^{th}$ embodiments of the present invention, a < shaped spring 18 is provided on the syringe tube 1, and is in conjunction with an actuator plate 182 at the latter's rear bottom, while a stop block 183 is provided at the front bottom portion of the actuator plate 182, More than two recesses 24 are formed on the protective cover 2 in the position on the same lengthwise line with the stop block 183 Here, a concaved trap 184 is formed at the front end bottom of the <shaped spring 18, while a billet 25 is formed at the rear end of the protective cover 2 in a position corresponding to the concaved trap 184 (see FIG. 28). Alternatively, a billet 185 is formed at the front end bottom of the <shaped spring 18, while a concaved trap 251 is formed at the rear end of the protective cover 2 in the position corresponding to the billet 185 as shown in FIG. 29.

Referring to FIG. 30 through FIG. 32, in the 20$^{th}$ to 22th embodiments of the present invention, the protective cover 2 is provided with the elastic hasp mechanism 23 which including the spring strap 231, the supporting stud 232, and the actuate plate 233. The supporting stud 232 is in contact with the front portion of the actuate plate 233, and the stop block 234 is formed at the rear bottom portion of the actuate plate 233. More than two recesses 19 are formed on the outer surface of the syringe tube 1 in the position on the same lengthwise line with the stop block 234 (see FIG. 30), or a protuberance 105 is formed on the outer surface of the syringe tube 1, and forms more than two recesses 10 on the outer surface of the syringe tube 1 along the extension line connecting the stop block 234 and the protuberance 105, besides, a concaved trap 184 is formed ahead of the protuberance 105, and a billet 25 is formed on the rear end of the protective cover 2 at the position facing against the concaved trap 184 (see FIG. 31). Alternatively, the position of the concaved trap and the billet can be interchanged, i.e., to form a billet 185 at the position of the concaved trap 184, and to form a concaved trap 251 at the position of the billet 25 as shown in FIG. 32.

Referring to FIG. 33 through FIG. 35, in the 23th to 25$^{th}$ embodiments of the present invention, an annular ring 104 is formed around the front end of the tube 1 instead of the guide rod formed along the outer surface of tube 1, and several guide pipes 10 are formed on the fringe of the annular ring 104 each of them being aligning to the corresponding sliding groove 226. Moreover, a tube enclosure 106 is covered over the tube 1, and several billets 185 are formed on the front tip of the tube enclosure 106, while several concaved traps 25 equal to number of, and facing against the billets 185 are formed on the rear end of the protective cover 2 (see FIG. 33). Besides, an elastic hasp mechanism 23 can be formed on the protective tube 2 with a stop block 234 formed on one end to couple with a recess 19 formed on the front end of the tube enclosure 106 in the position facing against the stop block 234 (see FIG. 33). Besides, the < shaped spring strap 18 may be provided on the syringe tube 1, and is in conjunction with the actuator plate 182 at the latter's rear bottom, while the stop block 183 is provided at the front bottom portion of the actuator plate 182. More than two recesses 24 are formed on the protective cover 2 in the position on the same lengthwise line with the stop blocks 183 (see FIG. 34). Alternatively, the billet 185 formed on the front end of the tube enclosure may be replaced with a concaved trap 184, and the concaved trap 25 may be replaced with a stop block 251 as shown in FIG. 35.

Figure 36:
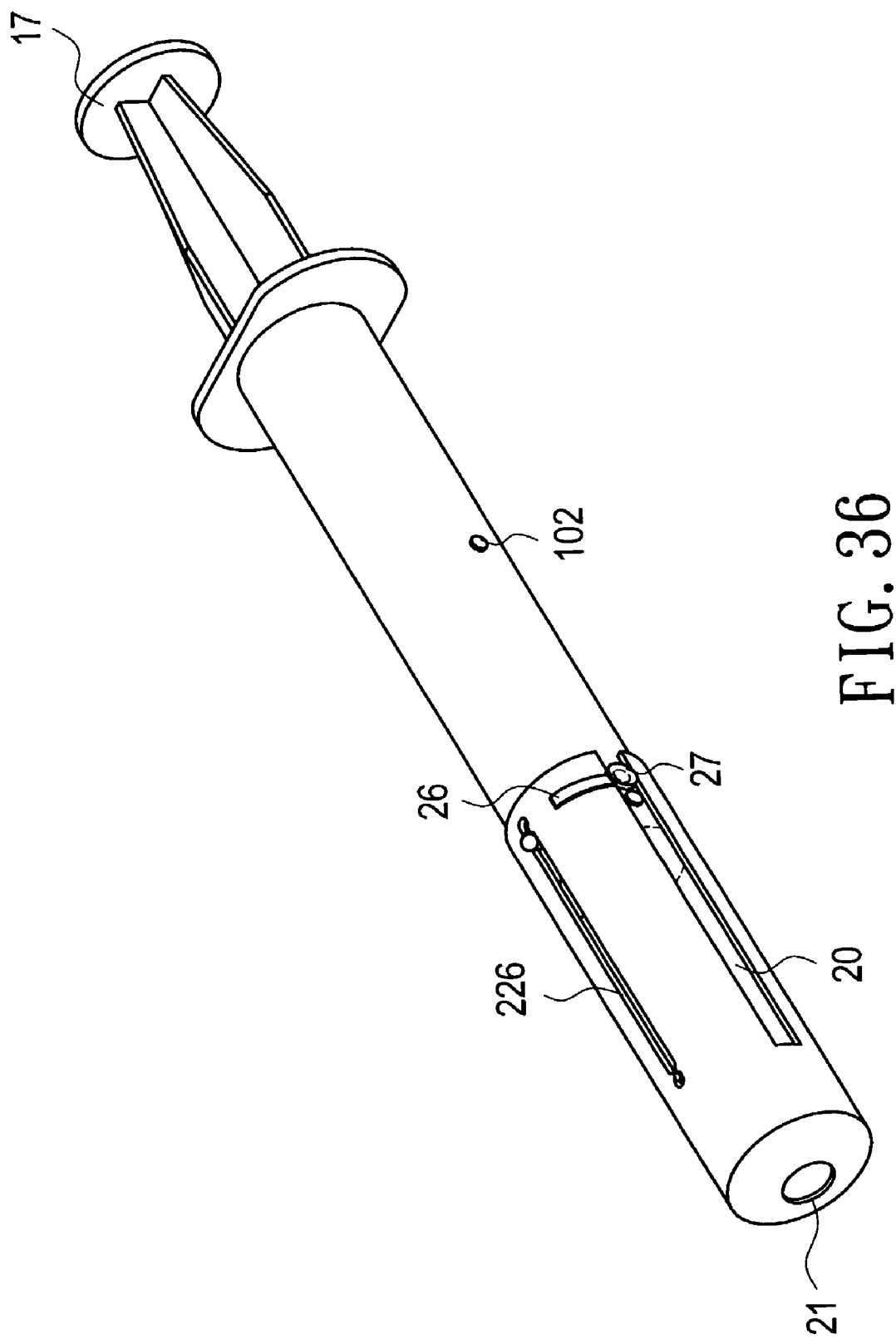
FIG. 36 is a three dimensional perspective view in a 26$^{th}$ embodiment of the present invention.

Referring to FIGS. 36 and 40, in the 26$^{th}$ and 30$^{th}$ embodiments of the present invention, a rectangular opening 226 is formed on the sliding plate 22 at the rear end of the protective cover 2, and two button hooks 102 are each formed on front and rear surface of the tube 1 respectively aligning to the rectangular opening 226. An elastic belt 26 connected with a button head 27 is provided on the surface of the protective cover 2. Before the operation of the injection takes place, the protective cover 2 is fixed to the rear portion of the tube 1 by pulling black the protective tube 2 and pressing the button head 27 into the rear button hook 102. Conversely, after the operation of the injection is finished, the protective cover 2 is pushed forwards by releasing the button head 27 from the rear button hook 102 and pressing the button head 27 into the front button hook 102 so as to fix the protective cover 2 to the front portion of tube 1 (see FIG. 36).

Alternatively, It may be as well providing only one button hook 102 on the front portion of the tube 1, and providing an elastic belt 26 together with a button head 27 on front and rear portions of the protective cover 2 respectively. By so, when the protective cover 2 slides to the rear portion of the tube 1, the button head 27 of the front elastic belt 26 snaps into the button hole 102 so as to fix the protective cover 2 to the rear portion of the tube 1. On the contrary, when the protective cover 2 slides to the front portion of the tube 1, the button head 27 of the rear elastic belt 26 snaps into the button hole 102 so as to fix the protective cover 2 to the front portion of the tube 1 thereby preventing hazardously emerging the needle out of the protective cover 2 as shown in FIG. 40.

Figure 37:
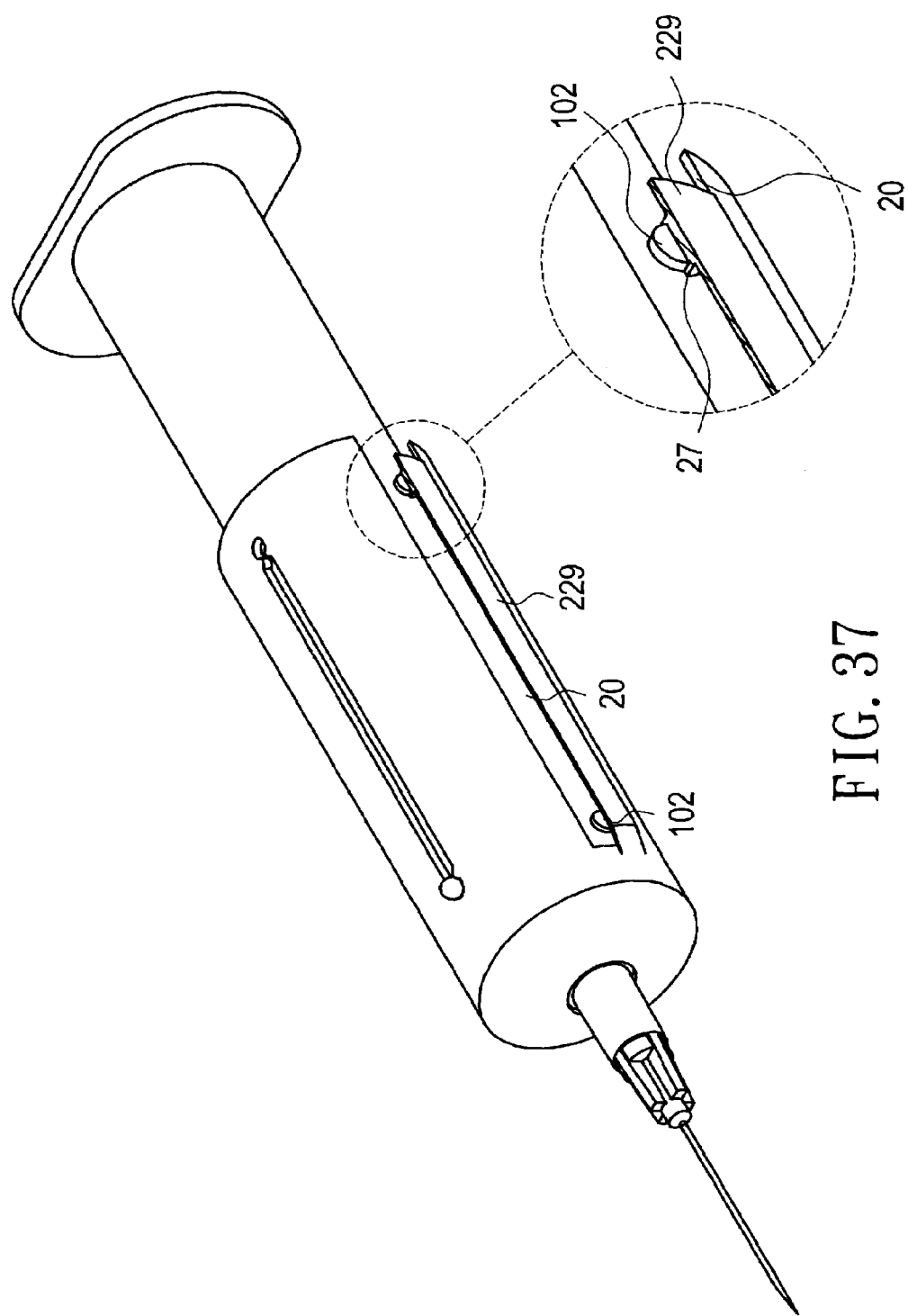
FIG. 37 is a three dimensional perspective view in a 27$^{th}$ embodiment of the present invention.
Figure 38:
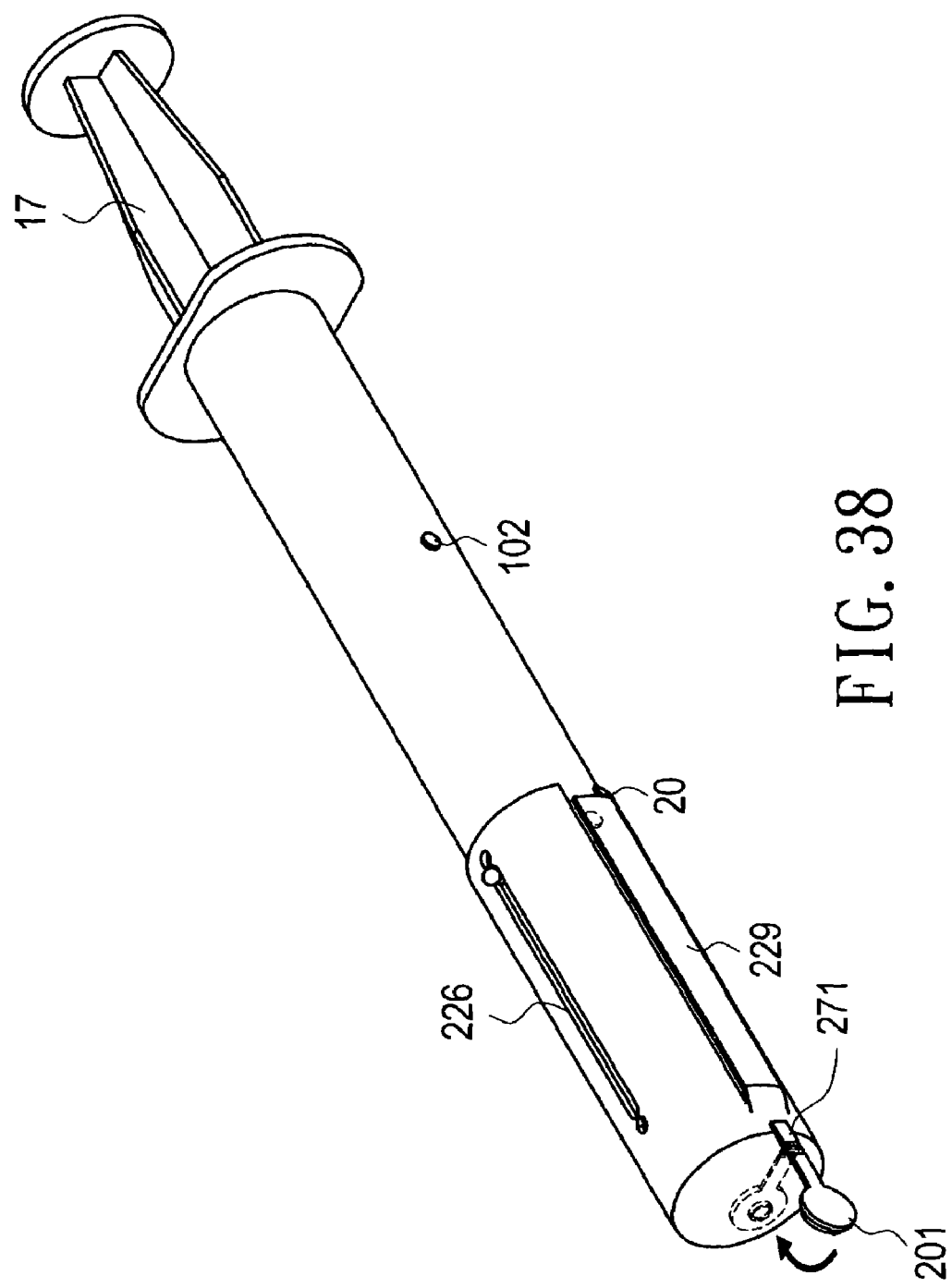
FIG. 38 is a three dimensional perspective view in a 28$^{th}$ embodiment of the present invention.
Figure 39:
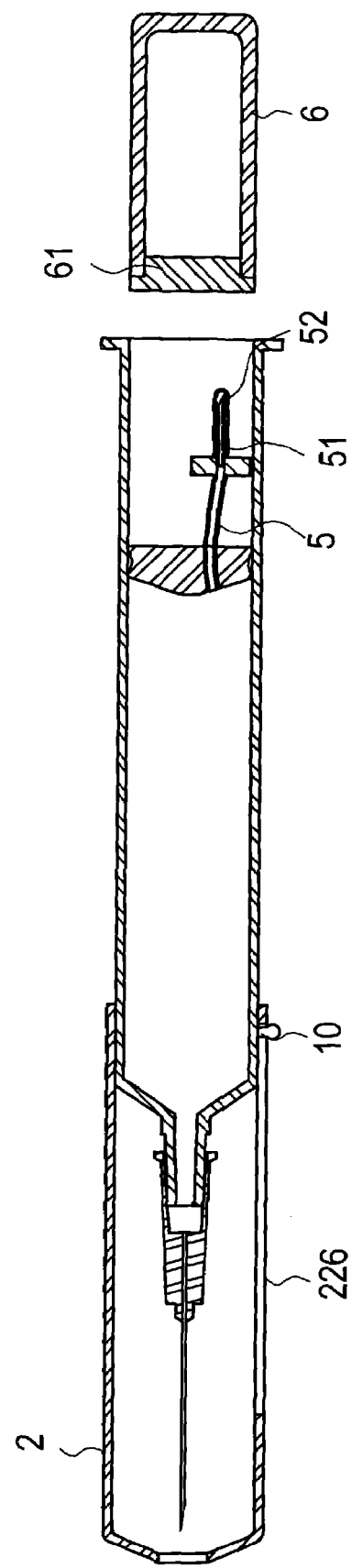
FIG. 39 is a longitudinal cross sectional view in a 29$^{th}$ embodiment of the present invention.

Referring to FIG. 37 through FIG. 39, in the 27$^{th}$ to 29$^{th}$ embodiment of the present invention, a rectangular opening 20 is formed on the sliding plate 22 at the rear end of the protective cover 2, and a button hook 102 is formed on the front and rear surfaces of the tube 1 respectively aligning to the rectangular opening 20. A reed 220 is formed on the protective tube 2 at the front and rear ends of the rectangular opening 20, and a button head 27 is formed on the rear inner side of the reed 229 (see FIG. 37). Besides, a folding hasp 271 with a hook-on head 201 is provided at the front head of the protective cover 2. Before operation of injection takes place, pull the protective cover 2 back, and press the button head 27 on the reed 229 to the piston 17 behind the tube 1. Meanwhile, a hose 5 passing through the plunger 12 and connected with a needle point 51 is provided in the cavity 11, and the needle point 51 is covered with an enclosure 52 made of a compressible substance. When it is desired to get blood sample, push an empty test tube 6 into the cavity 11 of the syringe tube 1, and pokes through a cork 61 covering the test tube 6 and the enclosure 52 with the needle point 51 so as to extract the blood sample from the patient body into the negative pressurized test tube 6. In case the blood sampling operation should be successively carried out, it is not necessary to draw back the injection needle from the patient body, only the thing has to be done is replacing the full blooded test tube 6 with a new empty one (FIG. 39)

Figure 42:
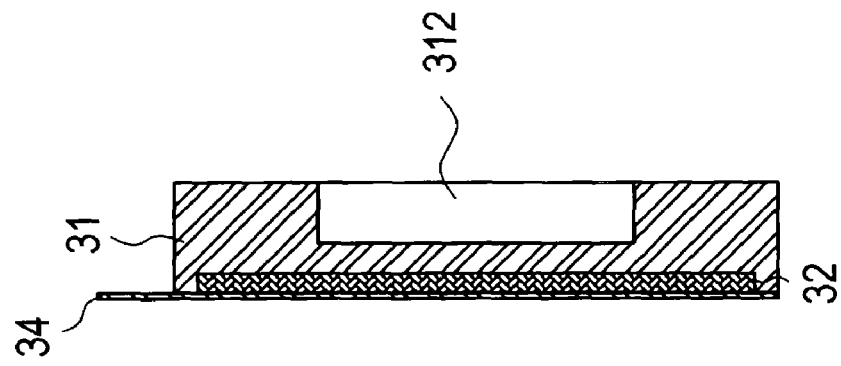
FIG. 42 is a side cross sectional view of the sterilizer in a fourth embodiment.
Figure 41:
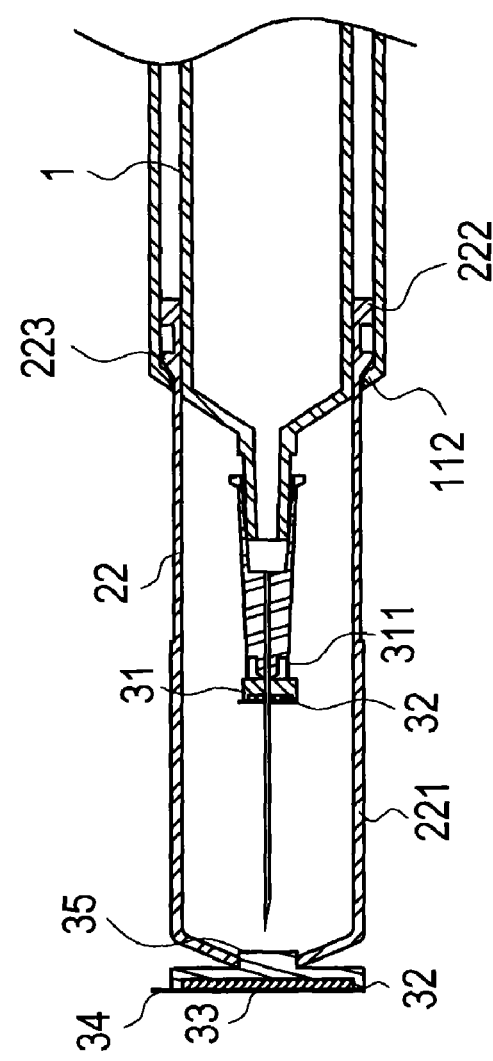
FIG. 41 is a view showing the operational principle of the sterilizer in a third embodiment.

Referring to FIGS. 41 and 42 which respectively show the operational principle of the sterilizer and a side cross sectional view of the sterilizer, in which the sterilizer 3 may be equipped at the tip of the needle of the syringe tube 1. The main body 31 of the sterilizer 3 has an joint portion 311 at the rear end thereof to adhere to, or to be jointed to the needle. When the present invention is to be operated either for extraction or injection, at first, the patient's body surface where syringe needle contacts is sterilized by the sterilizer 3, on the protective cover 2. After operation is finished, the medical staff may tear off a film 34 which is covering the sterilizer 3 and press the film 34 directly against the sterilizer 3 so as to stop blooding using the sterilized cotton 33. Besides, in the present invention, the plug 35 provided at the rear end of the sterilizer main body 31 can be replaced with a recessed joint portion 312 which can be coupled with the sterilizer main body 31.

Figure 43:
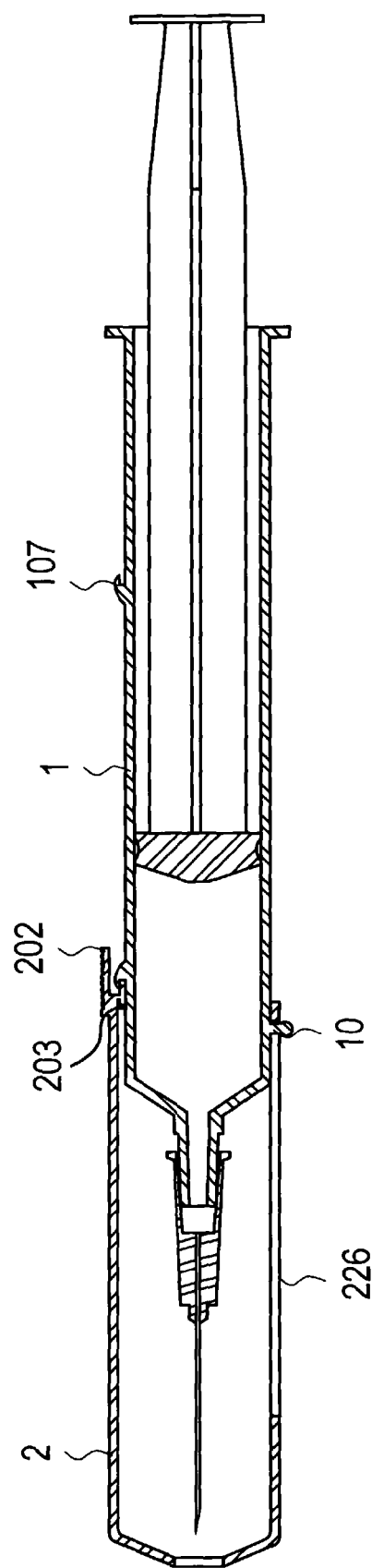
FIG. 43 is a longitudinal cross sectional view in a 31th embodiment of the present invention.

Referring to the 31th embodiment of the present invention shown in FIG. 43, there are more than one guide rods 10 provided along the outer edge of the tube 1, while several corresponding sliding grooves 226 are formed on the protective cover 2. Besides, two back-to-back faced humpbacked hook blocks 107 are coaxially formed on the outer surface of the tube 1, whereas a tap plate 202 is provided at the rear end of the protective cover 2 in a position along the same line with the two hook blocks 107. There is a hook joint 203 formed beneath the tap plate 202. With this structure, in the stand-by state the protective cover 2 is enclosed over the needle of the tube 1 and the hook joint 203 is engaged with the hook block 107. In starting operation of the present invention, at first, the protective cover 2 has to be slightly pushed forwards so as to separate the hook joint 203 from the hook block 107, then afterwards, the tap plate 202 is moved up and drawn back simultaneously so as to bring the bottom of the hook joint 203 passing through the hook block 107. Then push the protective cover 2 backwards, at this moment the hook joint 203 will slide over the hook block 107 to its rear end with the aid of the arcuate shaped back surface design of the hook block 107. Again, one step more, by pushing the protective cover forwards, the joint 203 is finally engaged with the hook block 107. Now, the operation of the present invention can be begun to carry out. After finishing the operation, the protective cover 2 is at first pushed backwards so as to release the hook joint 203 from the hook block 107, then by lifting up the tap plate 202 and pushing forwards so as to engage the hook joint 203 with the hook block 107 again thereby fixing the protective cover 2 to the front end of the tube 1 and enclosing the needle too. By doing so, there is no danger of emerging the needle.

Figure 44:
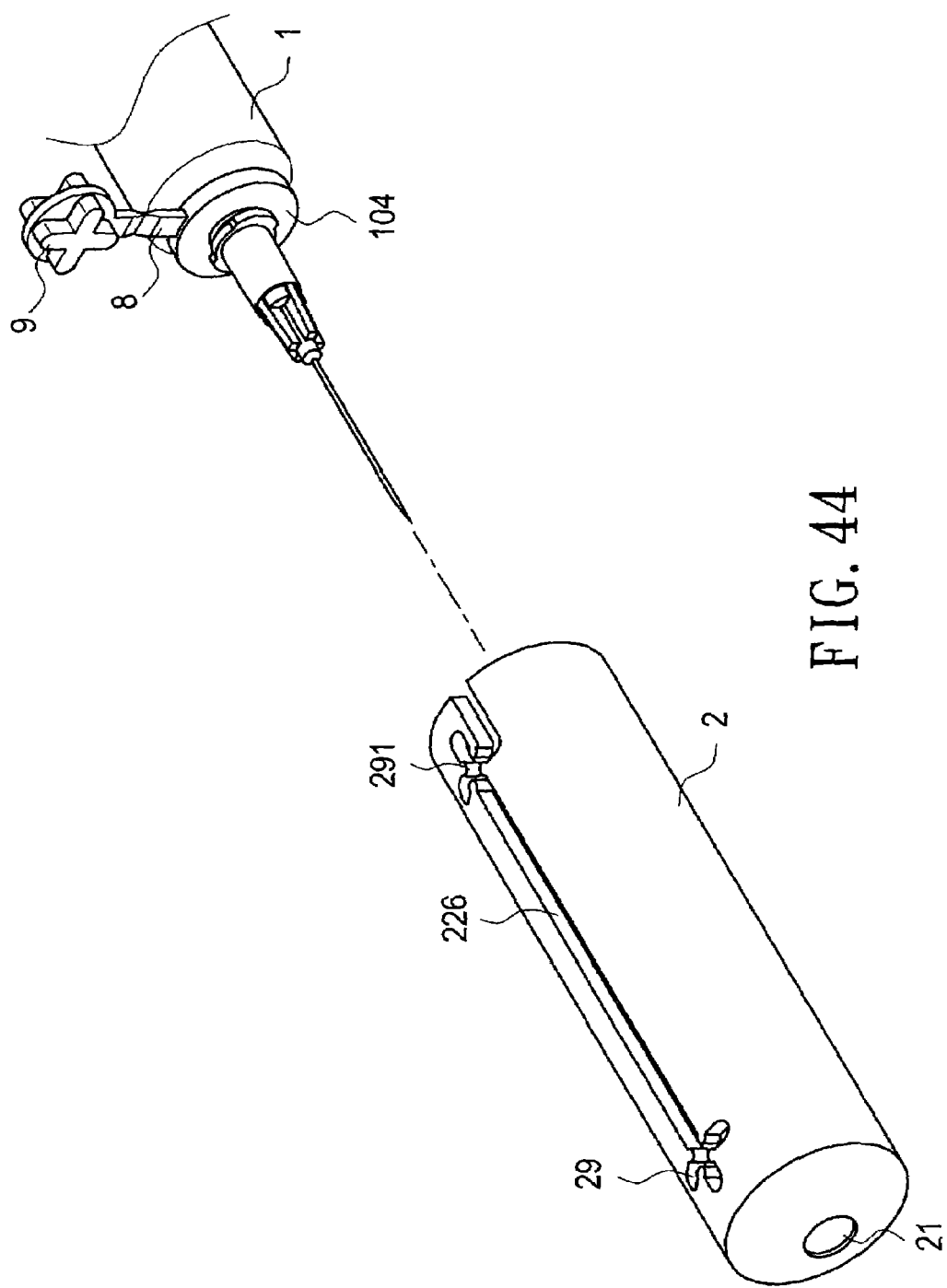
FIG. 44 is a three dimensional exploded view in a 32th embodiment of the present invention.

In the 32th embodiment of the present invention shown in FIG. 44, the sliding groove 226 formed on the protective cover 2 has a trap hole 29 perpendicular to the sliding groove 226 provided at one side or both sides at a position close to front and rear ends thereof, the trap bole 29 located at one side of the sliding groove 226's rear end is extended backwards and pierces through the protective cover 2, and a protuberance 291 is formed at the contacting point of each trap hole 29 with the sliding groove 226. An annular ring 104 is encircling around the front end of the tube 1 and having a flexed strap 8 connected with a stop block 9 to be trapped into the trap hole 29. Before operation of the present invention, the flexed strap 8 is penetrated through the protective cover 2 and moves to the sliding groove 226 from the position where the trap hole 29's rear end pierces the protective cover 2 such that the protective cover 2 is sleeved over the outer surface of the tube 1. The by trapping the stop block 9 into the trap hole 29, and pressing the stop block 9 firmly thereat with the protuberance 291, the protective cover 2 is stationary fixed at the front end of the tube 1. When beginning operation of the present invention, by releasing the stop block 9 from the trap hole 29 and pulling back the protective cover 2, and again trapping the stop block 9 into the trap hole 29, the protective cover 2 is now fixed at the rear end of the tube 1 ready for operation of the present invention. Alternatively, the flexed strap 8 may be directly equipped on the outer surface of the tube 1, and the trap hole 29 is not to penetrate the protective cover 2, but instead, the protective cover 2 is directly sleeved over the tube 1 during the fabrication process so as to cause the flexed strap 8 on the outer surface of tube 1 is emerged out along the sliding groove 226 of the protective cover 2.

Figure 45:
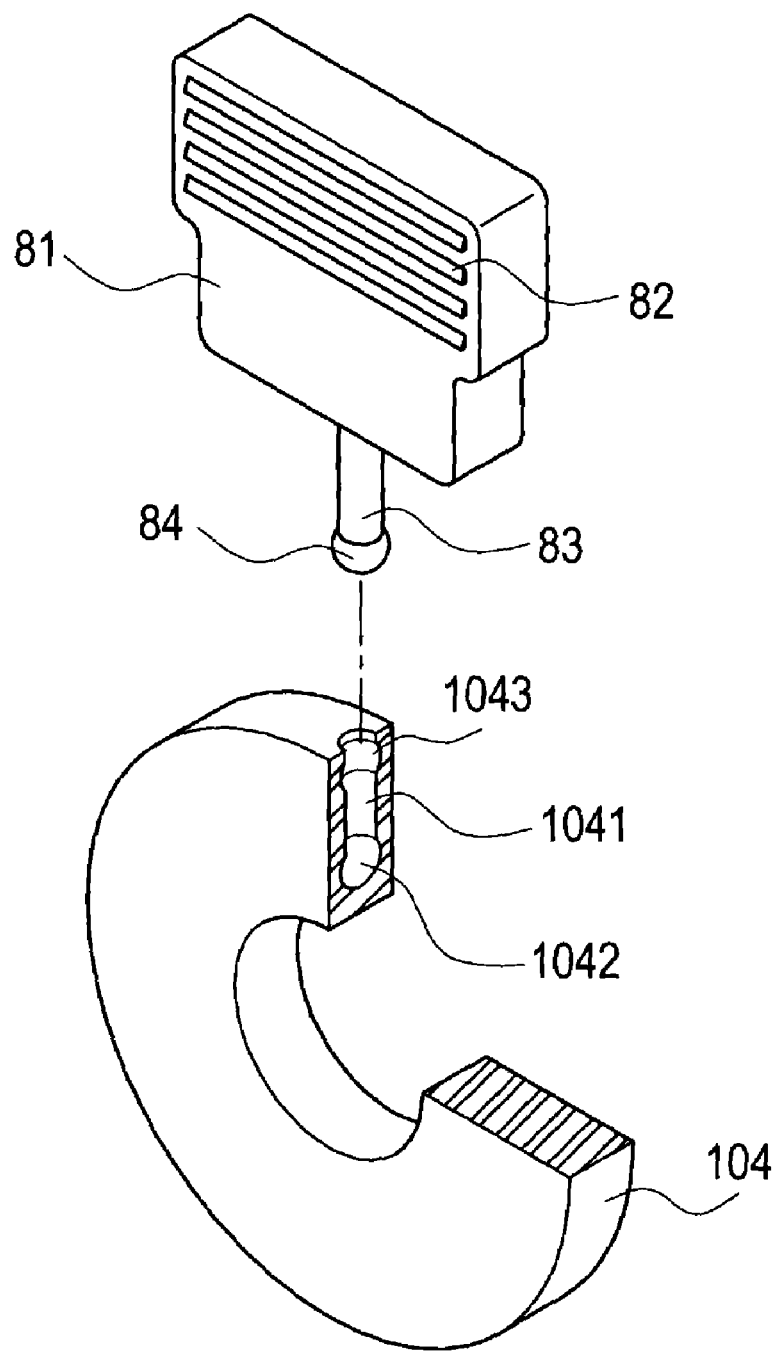
FIG. 45 is a three dimensional exploded view of the annular ring in a 32th embodiment of the present invention.

Further referring to FIG. 45, in this 32th embodiment showing the three dimensional cross sectional view of the annular ring 104, on the annular ring 104, the flexed strap 8 may be replaced with a stopper 81 having a grip 82 provided thereon, and a slide rod 83 is extended from its bottom. A button 84 is provided at the end of the slide rod 83, and an inlet slot 1041 having a fixed hole 1042 at its bottom is formed on the annular ring 104, a containment hole 1043 is further formed at the middle portion of the inlet slot 1041. In case the present invention is in the stand by state, the protective cover 2 is enclosing the needle at the front end of the tube 1, the stopper 81 is clogged in the trap hole 29 and is detained firmly by the protuberance 291. At this moment the button 84 is settled in the fixed hole 1042 of the annular ring 104. When starting the operation, the operator may grasp the grip 82 and pull up the stopper 81 with a finger so as to remove the button 84 to the containment hole 1043 of the annular ring 104, and next, by pulling the protective cover 2 backwards such that the protective cover 2 retracts to the rear end of the tube 1 with the aid of sliding motion of the slid rod 83 extended from the bottom of the stopper 81. At this moment, by removing the button 84 to settle in the fixed hole 1042 such that the stopper 81 is clogged in the trap hole 29 formed at the front end of the protective cover 2 thereby the protective cover 2 is fixed at the rear end of the tube 1 ready for apparatus of the present invention to operate either injection or extraction. Meanwhile, another slide rod 83 with a tip button 84 may be provided on the annular ring 104, and another inlet slot 1041 with a tip fixed hole 1042 and with a middle containment hole 1042 may be provided at the bottom of the stopper 81. alternatively, the slide rod 83 on the annular ring 104 may directly formed on the outer surface of the tube 1, or formed another inlet slot 1041 with a bottom fixed hole 1042, and a middle containment hole 1043, on the outer surface of the tube 1.

From the above description, it can be understood that the sterilized safety syringe of the present invention has several noteworthy advantages when compared with any conventional injection syringes, namely:

1. Operating medical staffs never have the fear of directly contamination from either injection drugs or patient body fluid.

2. The injection needle is perfectly protected by the protective cover and no possibility of inadvertent stinging the operator.

Although the description above contains many specificities, these should not be construed as limiting the scope of the invention but as merely providing illustration of some of the presently preferred embodiments of this invention. Thus the scope of the invention should be determined by the appended claims and there legal equivalents, rather than the examples given.

What is claimed is:

1. A sterilized safety syringe which is coupled with an air compressor using air feeding pipes for infusing drugs into the patient's body or extracting body fluid therefrom, comprising:

a syringe tube having a tip, an inner wall, an outer surface and an injection needle inserted at said tip, the inner wall of said tube defining a cavity and a guide slot formed between the outer surface and the inner wall of said syringe tube, said guide slot passing through a front wall surface of said syringe tube, and having a protrusion at a front end thereof, a plunger provided in said cavity and in close contact with the inner wall surface of said cavity, a rear end of said syringe tube being in a sealed state wherein said cavity and said guide slot are coupled with a plurality of air feeding pipes of said air compressor via an air conducting pipe;

a protective cover having a drilled hole at a front end thereof and the protective cover provided with a sliding plate at a rear end thereof, said sliding plate provided with a fixed part at a front portion thereof and an annular flange at its rear end; wherein said annular flange has a check fitting formed at a front edge and wherein said protective cover is actuated by said air compressor via one of said air conducting pipes;

a sterilizer having a main body with a pallet formed at a front end thereof, and a sterilized cotton swab being affixed to said pallet, a film formed at the front end of said main body for sealing said pallet, while a rear end of said main body forms a plug; wherein said sliding plate of said protective cover is fitted into said guide slot of said syringe tube and is forcibly in close contact with a wall of said guide slot with said annular flange; wherein said plug formed at the rear end of said sterilizer is plugged into said drilled hole of said protective cover.

2. The sterilized safety syringe as in claim 1, wherein said main body of said sterilizer and said plug are formed of a soft rubber or plastic substance.

\* \* \* \* \*